United States Patent [19]
Hall et al.

[11] Patent Number: 5,475,098
[45] Date of Patent: Dec. 12, 1995

[54] **DISTINCTIVE DNA SEQUENCE OF *E. COLI* 0157:H7 AND ITS USE FOR THE RAPID, SENSITIVE AND SPECIFIC DETECTION OF 0157:H7 AND OTHER ENTEROHEMORRHAGIC *E. COLI***

[75] Inventors: Robert H. Hall, Columbia, Md.; Jian-Guo Xu, Beijing, China

[73] Assignee: The United States of America as represented by the Department of Health and Human Services, Washington, D.C.

[21] Appl. No.: 258,188

[22] Filed: Jun. 14, 1994

[51] Int. Cl.⁶ .............................. C07H 17/00; A61K 5/00
[52] U.S. Cl. ...................... 536/23.7; 536/24.1; 536/24.2; 536/24.3; 536/24.32; 530/324
[58] Field of Search .................. 536/23.7, 24.1, 536/24.2, 24.3, 24.32; 530/324; 935/1, 11

[56] References Cited

U.S. PATENT DOCUMENTS 4,837,306  6/1989  Ling et al. ................. 530/387

*Primary Examiner*—W. Gary Jones
*Assistant Examiner*—Bradley L. Sisson
*Attorney, Agent, or Firm*—Townsend and Townsend and Crew

[57] ABSTRACT

The present invention provides isolated nucleic acid sequences corresponding to the hlyA gene, the hlyB gene and the intergenic region between the hlyA gene and the hlyB gene which are present in enterohemorrhagic *E. coli*. In addition, the present invention provides methods for detecting enterohemorrhagic *E. coli* by targeting the hlyA gene, the hlyB gene, the intergenic region between the hlyA and the hlyB genes, combinations thereof, or fragments thereof. Such methods rely on nucleic acid probes and amplification primers specific for subsequences of the hlyA gene, the hlyB gene, the intergenic region between the hlyA and the hlyB genes, combination thereof or, fragments thereof. As such, the present provides nucleic acid probes and amplification primers which can be used for the rapid, sensitive and specific amplification and detection of enterohemorrhagic *E. coli*. In addition, the present invention provides kits embracing the above aspects.

8 Claims, No Drawings targets for the rapid, sensitive and specific detection of enterohemorrhagic *E. coli* bacterial pathogens and, in particular, O157:H7 *E. coli*.

As such, in one aspect of the present invention, isolated nucleic acid sequences, corresponding to the hlyA gene, the hlyB gene and the intergenic region between the hlyA and hlyB genes, and novel peptides encoded by these nucleic acid sequences are provided. More particularly, the present invention provides an isolated DNA sequence encoding a peptide having the amino acid sequence of Sequence I.D. No. 2, and an isolated DNA sequence encoding a peptide having the amino acid sequence of Sequence I.D. No. 5. In addition, the present invention provides an isolated DNA sequence, the DNA sequence being the intergenic region between the hlyA gene and the hlyB gene and consisting of the nucleic acid sequence of Sequence I.D. No. 3. Moreover, the present invention provides an isolated, substantially purified DNA sequence specifically hybridizing, under stringent conditions, to a member selected from the group consisting of the hlyA gene, the hlyB gene, the intergenic region between the hlyA gene and the hlyB gene or, combinations or fragments thereof within an *E. coli* genomic or plasmid library, the DNA sequence consisting of a nucleic acid sequence selected from the group consisting of Sequence I.D. No. 1, Sequence I.D. No. 3, Sequence I.D. No. 4, combinations thereof or, fragments thereof.

In another aspect, the present invention provides a method for detecting the presence of enterohemorrhagic *E. coli* in a sample, the method comprising: (a) contacting the sample, under hybridization conditions, with a nucleic acid probe that selectively hybridizes to a member selected from the group consisting of the hlyA gene, the hlyB gene, the intergenic region between the hlyA gene and hlyB gene, or combinations or fragments thereof to form a hybridization complex; and (b) detecting the formation of the hybridization complex as an indication of the presence of enterohemorrhagic *E. coli* in the sample. In a preferred embodiment, the method further comprises prior to step (a), the amplification of a subsequence of the hlyA gene, the hlyB gene, the intergenic region between the hlyA and the hlyB genes, combinations thereof or, fragments thereof. The polymerase chain reaction, i.e., PCR, is a preferred method for amplifying the subsequence.

In yet another aspect of the present invention, a method for detecting the presence of enterohemorrhagic *E. coli* in a sample is provided, the method comprising: (a) lysing the target cells present in the sample by combining the sample with a lysis solution, thereby releasing nucleic acid from the target cells; (b) selecting a target, present in the target cells, from the group consisting of the hlyA gene, the hlyB gene, the intergenic region between the hlyA gene and the hlyB gene, or combinations thereof, and selecting a target nucleic acid sequence present in the target; (c) incubating the target nucleic acid sequence, under amplification conditions, with a pair of primers and a nucleic acid polymerase such that each primer is complementary to and hybridizes to one of two separated strands of the target nucleic acid sequence and the polymerase extends the primers to make fully double-stranded replicas of the target nucleic acid sequence; and (d) detecting amplified target nucleic acid as an indication of the presence of enterohemorrhagic *E. coli* in the sample.

In addition, the present invention provides amplification primers which can be used to selectively and effectively amplify a target region of the hlyA gene, the hlyB gene, the intergenic region between the hlyA and the hlyB genes, combinations thereof or, fragments thereof. Moreover, the present invention provides nucleic acid probes which can be used to selectively target, i.e., selectively hybridize to, the hlyA gene, the hlyB gene, the intergenic region between the hlyA and the hlyB genes, combinations thereof or, fragments thereof. It will be readily apparent to those of skill in the art, that amplification primers and nucleic acid probes, in addition to those set forth hereinbelow, can be made based on the nucleic acid sequences provided herein.

In a further aspect, the present invention provides a method for detecting the presence of enterohemorrhagic *E. coli* in a sample, the method comprising: (a) contacting the sample with a substantially purified immunoglobulin that specifically binds a peptide (e.g., HlyA or HlyB) encoded by a gene selected from the group consisting of the hlyA gene and the hlyB gene; and (b) detecting the bound immunoglobulin. In presently preferred embodiments, the peptide has the amino acid sequence of Sequence I.D. No. 2 or, alternatively, of Sequence I.D. No. 5.

In a final aspect, the present invention provides kits suitable for use in carrying out the PCR amplification and detection methods of the present invention.

The methods of the present invention provide for the rapid, sensitive and specific detection of enterohemorrhagic *E. coli*. In fact, of the over one-hundred positive control and negative control strains tested, no false positives and no false negatives have been found. The PCR amplification methods of the present invention have detected all EHEC strains tested, including a range of O157:H7 clinical isolates from the recent EHEC outbreak in the Pacific North-West. At least four patient isolates of O157:H7 from the Jack-In-The-Box Restaurant outbreak in Washington State (provided through the Washington State Department of Health), three O157:H7 strains from the Sizzler Restaurant outbreak in Oregon (provided by the Oregon State Department of Health) and three O157:H7 isolates from patients infected with raw milk (provided by the Oregon State Department of Health) were tested and found to be positive for hlyAB. Moreover, eighteen strains from various origins were tested and found to be positive. In addition, six strains obtained from the American Type Culture Collection (ATCC) were also tested. These strains included one which is slt-I and slt-II negative. Using the primers of the present invention, all six strains were recognized as EHECs. Furthermore, in a survey of EHEC strains from around the world, 7 out of 7 Japanese EHECs, 6 out of 6 Chinese EHECs, and 9 out of 9 American EHECs tested positive when using the PCR amplification methods of the present invention. These results unequivocally establish a direct correlation between the presence of the hlyA and hlyB genes and the disease symptoms of EC, HUS and MA, regardless of serogroup, slt-I, slt-II or uidA type or, O157:H7 serogroup. As such, using the methods of the present invention, enterohemorrhagic *E. coli* can be detected in a rapid, sensitive and highly specific manner.

Other features, objects and advantages of the invention and its preferred embodiments will become apparent from the detailed description which follows.

DEFINITIONS

"Nucleic acid," as used herein, refers to a deoxyribonucleic acid (DNA) or ribonucleic acid (RNA). More particularly, nucleic acid refers to a molecule comprised of two or more deoxyribonucleotides or ribonucleotides, preferably more than three, in either single- or double-stranded form, and unless otherwise limited, encompasses known analogs of natural nucleotides which can function in a manner similar to the naturally occurring nucleotides.

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 2278 base pairs
        ( B ) TYPE: nucleic acid
        ( C ) STRANDEDNESS: single
        ( D ) TOPOLOGY: linear ( i i ) MOLECULE TYPE: DNA (plasmid)

( i i i ) HYPOTHETICAL: NO ( i x ) FEATURE:
        ( A ) NAME/KEY: CDS
        ( B ) LOCATION: 2..2275

( i x ) FEATURE:
        ( A ) NAME/KEY: misc_feature
        ( B ) LOCATION: 1..2278
        ( D ) OTHER INFORMATION: /product="Peptide encoded by the hlyA gene"
        / standard_name="Nucleic acid sequence of hlyA gene"

( x i ) SEQUENCE DESCRIPTION: SEQ ID NO:1:

| | |
|---|---|
| A AGC TTT ATT CTG GGA AAC AGT GAC GCA CAT ACA GGA ACA AAA GCT<br>   Ser Phe Ile Leu Gly Asn Ser Asp Ala His Thr Gly Thr Lys Ala<br>    1             5                      10                      15 | 46 |
| GCA GCG GGT ATC GAA CTG ACA ACT CAG GTT CTT GGA AAT GTT GGT AAA<br>Ala Ala Gly Ile Glu Leu Thr Thr Gln Val Leu Gly Asn Val Gly Lys<br>                20                      25                      30 | 94 |
| GCT GTT TCG CAA TAT ATT CTG GCT CAG AGA ATG GCA CAG GGG TTA TCG<br>Ala Val Ser Gln Tyr Ile Leu Ala Gln Arg Met Ala Gln Gly Leu Ser<br>         35                      40                      45 | 142 |
| ACA ACA GCT GCA AGT GCG GGT CTG ATC ACA TCG GCT GTT ATG CTG GCT<br>Thr Thr Ala Ala Ser Ala Gly Leu Ile Thr Ser Ala Val Met Leu Ala<br>         50                      55                      60 | 190 |
| ATC AGT CCT CTT TCT TTC CTG GCT GCT GCA GAT AAA TTT GAG CGA GCT<br>Ile Ser Pro Leu Ser Phe Leu Ala Ala Ala Asp Lys Phe Glu Arg Ala<br>         65                      70                      75 | 238 |
| AAG CAG CTT GAA TCA TAT TCT GAA CGA TTT AAA AAA TTG AAT TAT GAA<br>Lys Gln Leu Glu Ser Tyr Ser Glu Arg Phe Lys Lys Leu Asn Tyr Glu<br>80                      85                      90                      95 | 286 |
| GGG GAT GCT TTA CTC GCA GCC TTT CAT AAA GAA ACC GGA GCT ATA GAT<br>Gly Asp Ala Leu Leu Ala Ala Phe His Lys Glu Thr Gly Ala Ile Asp<br>                100                     105                    110 | 334 |
| GCA GCC CTG ACA ACA ATA AAT ACT GTC CTG AGT TCT GTA TCT GCG GGA<br>Ala Ala Leu Thr Thr Ile Asn Thr Val Leu Ser Ser Val Ser Ala Gly<br>                115                     120                    125 | 382 |
| GTT AGT GCA GCC TCC AGT GCA TCC CTC ATA GGG GCC CCG ATA AGC ATG<br>Val Ser Ala Ala Ser Ser Ala Ser Leu Ile Gly Ala Pro Ile Ser Met<br>          130                     135                    140 | 430 |
| CTG GTG AGT GCA TTA ACC GGT ACG ATA TCT GGC ATT CTG GAA GCA TCA<br>Leu Val Ser Ala Leu Thr Gly Thr Ile Ser Gly Ile Leu Glu Ala Ser<br>      145                     150                    155 | 478 |
| AAA CAG GCT ATG TTT GAG CAC GTT GCA GAG AAA TTC GCT GCT CGG ATC<br>Lys Gln Ala Met Phe Glu His Val Ala Glu Lys Phe Ala Ala Arg Ile<br>160                      165                     170                  175 | 526 |
| AAT GAA TGG GAA AAG GAG CAT GGC AAA AAT TAT TTT GAG AAT GGA TAT<br>Asn Glu Trp Glu Lys Glu His Gly Lys Asn Tyr Phe Glu Asn Gly Tyr<br>                    180                     185                    190 | 574 |
| GAC GCA AGA CAT GCT GCG TTT TTA GAA GAC TCT CTG TCT TTG CTT GCT<br>Asp Ala Arg His Ala Ala Phe Leu Glu Asp Ser Leu Ser Leu Leu Ala<br>          195                     200                    205 | 622 |
| GAT TTT TCT CGT CAG CAT GCA GTA GAA AGA GCA GTC GCA ATA ACC CAG<br>Asp Phe Ser Arg Gln His Ala Val Glu Arg Ala Val Ala Ile Thr Gln<br>      210                     215                    220 | 670 |
| CAA CAT TGG GAT GAG AAG ATC GGT GAA CTT GCA GGC ATA ACC CGT AAT<br>Gln His Trp Asp Glu Lys Ile Gly Glu Leu Ala Gly Ile Thr Arg Asn<br>      225                     230                    235 | 718 |
| GCT GAT CGC AGT CAG AGT GGT AAG GCA TAT ATT AAT TAT CTG GAA AAT<br>Ala Asp Arg Ser Gln Ser Gly Lys Ala Tyr Ile Asn Tyr Leu Glu Asn<br>240                      245                     250                  255 | 766 |
| GGA GGG CTT TTA GAG GCT CAA CCG AAG GAG TTT ACA CAA CAA GTG TTT<br>Gly Gly Leu Leu Glu Ala Gln Pro Lys Glu Phe Thr Gln Gln Val Phe<br>                    260                     265                    270 | 814 |
| GAT CCT CAA AAA GGG ACC ATA GAC CTT TCA ACA GGT AAT GTA TCA AGT<br>Asp Pro Gln Lys Gly Thr Ile Asp Leu Ser Thr Gly Asn Val Ser Ser<br>          275                     280                    285 | 862 |
| GTT TTG ACA TTT ATA ACA CCA ACA TTT ACC CCA GGA GAA GAA GTT AGA<br>Val Leu Thr Phe Ile Thr Pro Thr Phe Thr Pro Gly Glu Glu Val Arg<br>                290                     295                    300 | 910 |
| GAA AGA AAA CAG AGT GGT AAA TAT GAA TAT ATG ACA TCT CTT ATT GTA<br>Glu Arg Lys Gln Ser Gly Lys Tyr Glu Tyr Met Thr Ser Leu Ile Val | 958 |

|  |  |  |  |  |  |  |  |  |  |  |  |  |  |  |  |
|---|---|---|---|---|---|---|---|---|---|---|---|---|---|---|---|
|  |  | 305 |  |  |  | 310 |  |  |  |  | 315 |  |  |  |  |
| AAT | GGT | AAG | GAT | ACA | TGG | TCT | GTA | AAA | GGC | ATA | AAA | AAT | CAT | AAA | GGT | 1006 |
| Asn | Gly | Lys | Asp | Thr | Trp | Ser | Val | Lys | Gly | Ile | Lys | Asn | His | Lys | Gly |
| 320 |  |  |  |  | 325 |  |  |  |  | 330 |  |  |  |  | 335 |
| GTA | TAT | GAT | TAT | TCA | AAA | TTG | ATT | CAG | TTT | GTT | GAA | AAG | AAT | AAC | AAA | 1054 |
| Val | Tyr | Asp | Tyr | Ser | Lys | Leu | Ile | Gln | Phe | Val | Glu | Lys | Asn | Asn | Lys |
|  |  |  |  | 340 |  |  |  |  | 345 |  |  |  |  | 350 |  |
| CAC | TAT | CAG | GCG | AGA | ATA | ATT | TCT | GAG | CTC | GGA | GAT | AAA | GAC | GAT | GTG | 1102 |
| His | Tyr | Gln | Ala | Arg | Ile | Ile | Ser | Glu | Leu | Gly | Asp | Lys | Asp | Asp | Val |
|  |  |  | 355 |  |  |  |  | 360 |  |  |  |  | 365 |  |  |
| GTT | TAT | TCT | GGA | GCA | GGC | TCA | TCA | GAA | GTA | TTT | GCT | GGT | GAA | GGT | TAT | 1150 |
| Val | Tyr | Ser | Gly | Ala | Gly | Ser | Ser | Glu | Val | Phe | Ala | Gly | Glu | Gly | Tyr |
|  |  | 370 |  |  |  |  | 375 |  |  |  |  | 380 |  |  |  |
| GAT | ACC | GTA | TCT | TAT | AAT | AAG | ACG | GAT | GTT | GGT | AAA | CTA | ACA | ATT | GAT | 1198 |
| Asp | Thr | Val | Ser | Tyr | Asn | Lys | Thr | Asp | Val | Gly | Lys | Leu | Thr | Ile | Asp |
|  | 385 |  |  |  |  | 390 |  |  |  |  | 395 |  |  |  |  |
| GCA | ACA | GGA | GCA | TCA | AAA | CCT | GGT | GAG | TAT | ATA | GTT | TCA | AAA | AAT | ATG | 1246 |
| Ala | Thr | Gly | Ala | Ser | Lys | Pro | Gly | Glu | Tyr | Ile | Val | Ser | Lys | Asn | Met |
| 400 |  |  |  |  | 405 |  |  |  |  | 410 |  |  |  |  | 415 |
| TAT | GGT | GAC | GTG | AAG | GTA | TTG | CAG | GAA | GTC | GTT | AAG | GAA | CAG | GAG | GTG | 1294 |
| Tyr | Gly | Asp | Val | Lys | Val | Leu | Gln | Glu | Val | Val | Lys | Glu | Gln | Glu | Val |
|  |  |  |  | 420 |  |  |  |  | 425 |  |  |  |  | 430 |  |
| TCA | GTA | GGG | AAG | CGA | ACA | GAG | AAA | ATA | CAA | TAT | CGT | GAT | TTT | GAA | TTC | 1342 |
| Ser | Val | Gly | Lys | Arg | Thr | Glu | Lys | Ile | Gln | Tyr | Arg | Asp | Phe | Glu | Phe |
|  |  |  | 435 |  |  |  |  | 440 |  |  |  |  | 445 |  |  |
| AGA | ACC | GGT | GGA | ATT | CCT | TAT | GAT | GTA | ATA | GAT | AAT | CTT | CAT | TCT | GTT | 1390 |
| Arg | Thr | Gly | Gly | Ile | Pro | Tyr | Asp | Val | Ile | Asp | Asn | Leu | His | Ser | Val |
|  |  | 450 |  |  |  |  | 455 |  |  |  |  | 460 |  |  |  |
| GAA | GAG | CTC | ATT | GGC | GGA | AAA | CAT | GAT | GAT | GAA | TTC | AAA | GGC | GGT | AAG | 1438 |
| Glu | Glu | Leu | Ile | Gly | Gly | Lys | His | Asp | Asp | Glu | Phe | Lys | Gly | Gly | Lys |
| 465 |  |  |  |  | 470 |  |  |  |  | 475 |  |  |  |  |  |
| TTT | AAT | GAT | ATA | TTC | CAT | GGC | GCA | GAT | GGG | AAC | GAT | TAT | ATC | GAA | GGT | 1486 |
| Phe | Asn | Asp | Ile | Phe | His | Gly | Ala | Asp | Gly | Asn | Asp | Tyr | Ile | Glu | Gly |
| 480 |  |  |  |  | 485 |  |  |  |  | 490 |  |  |  |  | 495 |
| AAT | TAT | GGT | AAT | GAT | CGA | CTA | TAC | GGC | GAT | GAT | GGG | GAT | GAT | TAT | ATA | 1534 |
| Asn | Tyr | Gly | Asn | Asp | Arg | Leu | Tyr | Gly | Asp | Asp | Gly | Asp | Asp | Tyr | Ile |
|  |  |  |  | 500 |  |  |  |  | 505 |  |  |  |  | 510 |  |
| TCC | GGA | GGA | CAG | GGA | GAC | GAC | CAG | TTA | TTT | GGT | GGT | AGT | GGA | AAC | GAT | 1582 |
| Ser | Gly | Gly | Gln | Gly | Asp | Asp | Gln | Leu | Phe | Gly | Gly | Ser | Gly | Asn | Asp |
|  |  |  | 515 |  |  |  |  | 520 |  |  |  |  | 525 |  |  |
| AAA | TTG | AGT | GGA | GGG | GAT | GGT | AAT | AAT | TAT | CTG | ACA | GGA | GGA | AGC | GGT | 1630 |
| Lys | Leu | Ser | Gly | Gly | Asp | Gly | Asn | Asn | Tyr | Leu | Thr | Gly | Gly | Ser | Gly |
|  |  | 530 |  |  |  |  | 535 |  |  |  |  | 540 |  |  |  |
| AAT | GAT | GAG | CTT | CAG | GCA | CAC | GGA | GCT | TAT | AAT | ATT | CTG | TCA | GGT | GGT | 1678 |
| Asn | Asp | Glu | Leu | Gln | Ala | His | Gly | Ala | Tyr | Asn | Ile | Leu | Ser | Gly | Gly |
|  | 545 |  |  |  |  | 550 |  |  |  |  | 555 |  |  |  |  |
| ACT | GGT | GAT | GAT | AAA | CTT | TAT | GGT | GGT | GGT | ATT | GAT | CTT | CTG | GAT | 1726 |
| Thr | Gly | Asp | Asp | Lys | Leu | Tyr | Gly | Gly | Gly | Ile | Asp | Leu | Leu | Asp |
| 560 |  |  |  |  | 565 |  |  |  |  | 570 |  |  |  |  | 575 |
| GGA | GGG | GAA | GGT | AAT | GAC | TAT | CTG | AAT | GGT | GGT | TTT | GGT | AAT | GAT | ATT | 1774 |
| Gly | Gly | Glu | Gly | Asn | Asp | Tyr | Leu | Asn | Gly | Gly | Phe | Gly | Asn | Asp | Ile |
|  |  |  |  | 580 |  |  |  |  | 585 |  |  |  |  | 590 |  |
| TAT | GTT | TAT | GGG | CAA | AAC | TAT | GGT | CAT | CAT | ACA | ATT | GCA | GAT | GAA | GGA | 1822 |
| Tyr | Val | Tyr | Gly | Gln | Asn | Tyr | Gly | His | His | Thr | Ile | Ala | Asp | Glu | Gly |
|  |  |  | 595 |  |  |  |  | 600 |  |  |  |  | 605 |  |  |
| GGT | AAA | GGA | GAT | CGT | TTG | CAC | TTA | TCT | GAT | ATT | AGC | TTT | GAT | GAT | ATC | 1870 |
| Gly | Lys | Gly | Asp | Arg | Leu | His | Leu | Ser | Asp | Ile | Ser | Phe | Asp | Asp | Ile |
|  |  | 610 |  |  |  |  | 615 |  |  |  |  | 620 |  |  |  |
| GCA | TTT | AAG | AGA | GTT | GGA | AAT | GAT | CTT | ATC | ATG | AAT | AAA | GCC | ATT | AAT | 1918 |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Ala | Phe | Lys | Arg | Val | Gly | Asn | Asp | Leu | Ile | Met | Asn | Lys | Ala | Ile | Asn |      |
|     | 625 |     |     |     | 630 |     |     |     |     | 635 |     |     |     |     |     |      |
| GGT | GTA | CTT | TCA | TTT | AAT | GAG | TCA | AAT | GAT | GTC | AAT | GGG | ATA | ACA | TTT | 1966 |
| Gly | Val | Leu | Ser | Phe | Asn | Glu | Ser | Asn | Asp | Val | Asn | Gly | Ile | Thr | Phe |      |
| 640 |     |     |     |     | 645 |     |     |     |     | 650 |     |     |     |     | 655 |      |
| AAA | AAC | TGG | TTT | GCG | AAA | GAT | GCC | TCA | GGA | GCA | GAT | AAT | CAT | CTT | GTT | 2014 |
| Lys | Asn | Trp | Phe | Ala | Lys | Asp | Ala | Ser | Gly | Ala | Asp | Asn | His | Leu | Val |      |
|     |     |     |     | 660 |     |     |     |     | 665 |     |     |     |     | 670 |     |      |
| GAG | GTT | ATA | ACA | GAT | AAA | GAT | GGT | CGA | GAG | ATA | AAA | GTT | GAT | AAG | ATA | 2062 |
| Glu | Val | Ile | Thr | Asp | Lys | Asp | Gly | Arg | Glu | Ile | Lys | Val | Asp | Lys | Ile |      |
|     |     |     | 675 |     |     |     |     | 680 |     |     |     |     | 685 |     |     |      |
| CCT | CAT | AAT | AAT | AAT | GAA | CGG | TCA | GGT | TAT | ATA | AAA | GCC | AGT | AAT | ATA | 2110 |
| Pro | His | Asn | Asn | Asn | Glu | Arg | Ser | Gly | Tyr | Ile | Lys | Ala | Ser | Asn | Ile |      |
|     |     | 690 |     |     |     |     | 695 |     |     |     |     | 700 |     |     |     |      |
| GCA | TCT | GAA | AAA | AAC | ATG | GTT | AAT | ATC | ACC | AGT | GTT | GCC | AAT | GAT | ATT | 2158 |
| Ala | Ser | Glu | Lys | Asn | Met | Val | Asn | Ile | Thr | Ser | Val | Ala | Asn | Asp | Ile |      |
|     | 705 |     |     |     |     | 710 |     |     |     |     | 715 |     |     |     |     |      |
| AAT | AAG | ATT | ATT | TCT | TCA | GTT | TCA | GGG | TTC | GAT | TCA | GGT | GAT | GAA | CGA | 2206 |
| Asn | Lys | Ile | Ile | Ser | Ser | Val | Ser | Gly | Phe | Asp | Ser | Gly | Asp | Glu | Arg |      |
| 720 |     |     |     |     | 725 |     |     |     |     | 730 |     |     |     |     | 735 |      |
| TTA | GCA | TCT | TTA | TAT | AAT | TTA | TCC | TTA | CAT | CAA | AAC | AAC | ACA | CAC | TCA | 2254 |
| Leu | Ala | Ser | Leu | Tyr | Asn | Leu | Ser | Leu | His | Gln | Asn | Asn | Thr | His | Ser |      |
|     |     |     |     | 740 |     |     |     |     | 745 |     |     |     |     | 750 |     |      |
| ACA | ACT | TTA | ACG | ACA | ACT | GTC | TGA |     |     |     |     |     |     |     |     | 2278 |
| Thr | Thr | Leu | Thr | Thr | Thr | Val |     |     |     |     |     |     |     |     |     |      |
|     |     | 755 |     |     |     |     |     |     |     |     |     |     |     |     |     |      |

( 2 ) INFORMATION FOR SEQ ID NO:2:

( i ) SEQUENCE CHARACTERISTICS:
        ( A ) LENGTH: 758 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

|     |     |     |     |     |     |     |     |     |     |     |     |     |     |     |
|-----|-----|-----|-----|-----|-----|-----|-----|-----|-----|-----|-----|-----|-----|-----|
| Ser | Phe | Ile | Leu | Gly | Asn | Ser | Asp | Ala | His | Thr | Gly | Thr | Lys | Ala | Ala |
| 1   |     |     |     | 5   |     |     |     |     | 10  |     |     |     |     | 15  |
| Ala | Gly | Ile | Glu | Leu | Thr | Thr | Gln | Val | Leu | Gly | Asn | Val | Gly | Lys | Ala |
|     |     |     | 20  |     |     |     |     | 25  |     |     |     |     | 30  |     |
| Val | Ser | Gln | Tyr | Ile | Leu | Ala | Gln | Arg | Met | Ala | Gln | Gly | Leu | Ser | Thr |
|     |     | 35  |     |     |     |     | 40  |     |     |     |     | 45  |     |     |
| Thr | Ala | Ala | Ser | Ala | Gly | Leu | Ile | Thr | Ser | Ala | Val | Met | Leu | Ala | Ile |
|     | 50  |     |     |     |     | 55  |     |     |     |     | 60  |     |     |     |
| Ser | Pro | Leu | Ser | Phe | Leu | Ala | Ala | Asp | Lys | Phe | Glu | Arg | Ala | Lys |
| 65  |     |     |     |     | 70  |     |     |     |     | 75  |     |     |     |     | 80  |
| Gln | Leu | Glu | Ser | Tyr | Ser | Glu | Arg | Phe | Lys | Lys | Leu | Asn | Tyr | Glu | Gly |
|     |     |     |     | 85  |     |     |     |     | 90  |     |     |     |     | 95  |
| Asp | Ala | Leu | Leu | Ala | Ala | Phe | His | Lys | Glu | Thr | Gly | Ala | Ile | Asp | Ala |
|     |     |     | 100 |     |     |     |     | 105 |     |     |     |     | 110 |     |
| Ala | Leu | Thr | Thr | Ile | Asn | Thr | Val | Leu | Ser | Ser | Val | Ser | Ala | Gly | Val |
|     |     | 115 |     |     |     |     | 120 |     |     |     |     | 125 |     |     |
| Ser | Ala | Ala | Ser | Ser | Ala | Ser | Leu | Ile | Gly | Ala | Pro | Ile | Ser | Met | Leu |
|     | 130 |     |     |     |     | 135 |     |     |     |     | 140 |     |     |     |
| Val | Ser | Ala | Leu | Thr | Gly | Thr | Ile | Ser | Gly | Ile | Leu | Glu | Ala | Ser | Lys |
| 145 |     |     |     |     | 150 |     |     |     |     | 155 |     |     |     |     | 160 |
| Gln | Ala | Met | Phe | Glu | His | Val | Ala | Glu | Lys | Phe | Ala | Ala | Arg | Ile | Asn |
|     |     |     |     | 165 |     |     |     |     | 170 |     |     |     |     | 175 |

-continued

| | | | | | | | | | | | | | | | |
|---|---|---|---|---|---|---|---|---|---|---|---|---|---|---|---|
| Glu | Trp | Glu | Lys 180 | Glu | His | Gly | Lys 185 | Asn | Tyr | Phe | Glu | Asn 190 | Gly | Tyr | Asp |
| Ala | Arg | His 195 | Ala | Ala | Phe | Leu 200 | Glu | Asp | Ser | Leu | Ser 205 | Leu | Leu | Ala | Asp |
| Phe | Ser 210 | Arg | Gln | His | Ala | Val 215 | Glu | Arg | Ala | Val | Ala 220 | Ile | Thr | Gln | Gln |
| His 225 | Trp | Asp | Glu | Lys | Ile 230 | Gly | Glu | Leu | Ala | Gly 235 | Ile | Thr | Arg | Asn | Ala 240 |
| Asp | Arg | Ser | Gln | Ser 245 | Gly | Lys | Ala | Tyr | Ile 250 | Asn | Tyr | Leu | Glu | Asn 255 | Gly |
| Gly | Leu | Leu | Glu 260 | Ala | Gln | Pro | Lys | Glu 265 | Phe | Thr | Gln | Gln | Val 270 | Phe | Asp |
| Pro | Gln | Lys 275 | Gly | Thr | Ile | Asp | Leu 280 | Ser | Thr | Gly | Asn | Val 285 | Ser | Ser | Val |
| Leu | Thr 290 | Phe | Ile | Thr | Pro | Thr 295 | Phe | Thr | Pro | Gly | Glu 300 | Glu | Val | Arg | Glu |
| Arg 305 | Lys | Gln | Ser | Gly | Lys 310 | Tyr | Glu | Tyr | Met | Thr 315 | Ser | Leu | Ile | Val | Asn 320 |
| Gly | Lys | Asp | Thr | Trp 325 | Ser | Val | Lys | Gly | Ile 330 | Lys | Asn | His | Lys | Gly 335 | Val |
| Tyr | Asp | Tyr | Ser 340 | Lys | Leu | Ile | Gln | Phe 345 | Val | Glu | Lys | Asn | Asn 350 | Lys | His |
| Tyr | Gln | Ala 355 | Arg | Ile | Ile | Ser | Glu 360 | Leu | Gly | Asp | Lys | Asp 365 | Val | Val |
| Tyr | Ser 370 | Gly | Ala | Gly | Ser | Ser 375 | Glu | Val | Phe | Ala | Gly 380 | Glu | Gly | Tyr | Asp |
| Thr 385 | Val | Ser | Tyr | Asn | Lys 390 | Thr | Asp | Val | Gly | Lys 395 | Leu | Thr | Ile | Asp | Ala 400 |
| Thr | Gly | Ala | Ser | Lys 405 | Pro | Gly | Glu | Tyr | Ile 410 | Val | Ser | Lys | Asn | Met 415 | Tyr |
| Gly | Asp | Val | Lys 420 | Val | Leu | Gln | Glu | Val 425 | Val | Lys | Glu | Gln | Glu 430 | Val | Ser |
| Val | Gly | Lys 435 | Arg | Thr | Glu | Lys | Ile 440 | Gln | Tyr | Arg | Asp | Phe 445 | Glu | Phe | Arg |
| Thr | Gly 450 | Gly | Ile | Pro | Tyr | Asp 455 | Val | Ile | Asp | Asn | Leu 460 | His | Ser | Val | Glu |
| Glu 465 | Leu | Ile | Gly | Gly | Lys 470 | His | Asp | Asp | Glu | Phe 475 | Lys | Gly | Gly | Lys | Phe 480 |
| Asn | Asp | Ile | Phe | His 485 | Gly | Ala | Asp | Gly | Asn 490 | Asp | Tyr | Ile | Glu | Gly 495 | Asn |
| Tyr | Gly | Asn | Asp 500 | Arg | Leu | Tyr | Gly | Asp 505 | Asp | Gly | Asp | Asp | Tyr 510 | Ile | Ser |
| Gly | Gly | Gln 515 | Gly | Asp | Asp | Gln | Leu 520 | Phe | Gly | Gly | Ser | Gly 525 | Asn | Asp | Lys |
| Leu | Ser 530 | Gly | Gly | Asp | Gly | Asn 535 | Asn | Tyr | Leu | Thr | Gly 540 | Gly | Ser | Gly | Asn |
| Asp 545 | Glu | Leu | Gln | Ala | His 550 | Gly | Ala | Tyr | Asn | Ile 555 | Leu | Ser | Gly | Gly | Thr 560 |
| Gly | Asp | Asp | Lys | Leu 565 | Tyr | Gly | Gly | Gly | Ile 570 | Asp | Leu | Leu | Asp | Gly 575 |
| Gly | Glu | Gly | Asn 580 | Asp | Tyr | Leu | Asn | Gly 585 | Gly | Phe | Gly | Asn | Asp 590 | Ile | Tyr |

| Val | Tyr | Gly | Gln | Asn | Tyr | Gly | His | His | Thr | Ile | Ala | Asp | Glu | Gly | Gly |
| | | 595 | | | | 600 | | | | | 605 | | | | |

| Lys | Gly | Asp | Arg | Leu | His | Leu | Ser | Asp | Ile | Ser | Phe | Asp | Asp | Ile | Ala |
| | 610 | | | | 615 | | | | | | 620 | | | | |

| Phe | Lys | Arg | Val | Gly | Asn | Asp | Leu | Ile | Met | Asn | Lys | Ala | Ile | Asn | Gly |
| 625 | | | | | 630 | | | | | 635 | | | | | 640 |

| Val | Leu | Ser | Phe | Asn | Glu | Ser | Asn | Asp | Val | Asn | Gly | Ile | Thr | Phe | Lys |
| | | | | 645 | | | | | 650 | | | | | 655 | |

| Asn | Trp | Phe | Ala | Lys | Asp | Ala | Ser | Gly | Ala | Asp | Asn | His | Leu | Val | Glu |
| | | | 660 | | | | | 665 | | | | | 670 | | |

| Val | Ile | Thr | Asp | Lys | Asp | Gly | Arg | Glu | Ile | Lys | Val | Asp | Lys | Ile | Pro |
| | | 675 | | | | | 680 | | | | | 685 | | | |

| His | Asn | Asn | Asn | Glu | Arg | Ser | Gly | Tyr | Ile | Lys | Ala | Ser | Asn | Ile | Ala |
| | 690 | | | | | 695 | | | | | 700 | | | | |

| Ser | Glu | Lys | Asn | Met | Val | Asn | Ile | Thr | Ser | Val | Ala | Asn | Asp | Ile | Asn |
| 705 | | | | | 710 | | | | | 715 | | | | | 720 |

| Lys | Ile | Ile | Ser | Ser | Val | Ser | Gly | Phe | Asp | Ser | Gly | Asp | Glu | Arg | Leu |
| | | | | 725 | | | | | 730 | | | | | 735 | |

| Ala | Ser | Leu | Tyr | Asn | Leu | Ser | Leu | His | Gln | Asn | Asn | Thr | His | Ser | Thr |
| | | | 740 | | | | | 745 | | | | | 750 | | |

| Thr | Leu | Thr | Thr | Thr | Val |
| | | 755 | | | |

(2) INFORMATION FOR SEQ ID NO:3:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (plasmid)

(iii) HYPOTHETICAL: NO (ix) FEATURE:
        (A) NAME/KEY: misc_feature
        (B) LOCATION: 1..49
        (D) OTHER INFORMATION: /standard_name="Nucleic acid
            sequence of intergenic region"

(xi) SEQUENCE DESCRIPTION: SEQ ID NO:3:

GACTAAAAGA GGAGGTGATG GCCATTCCAG GAGGAATGGT CATCGTTAT    49

(2) INFORMATION FOR SEQ ID NO:4:

(i) SEQUENCE CHARACTERISTICS:
        (A) LENGTH: 994 base pairs
        (B) TYPE: nucleic acid
        (C) STRANDEDNESS: single
        (D) TOPOLOGY: linear (ii) MOLECULE TYPE: DNA (plasmid)

(iii) HYPOTHETICAL: NO (ix) FEATURE:
        (A) NAME/KEY: CDS
        (B) LOCATION: 1..993

(ix) FEATURE:
        (A) NAME/KEY: misc_feature
        (B) LOCATION: 1..994
        (D) OTHER INFORMATION: /product="Peptide encoded by the
            hlyB gene"
        / standard_name="Nucleic acid sequence of the hlyB gene"

( x i ) SEQUENCE DESCRIPTION: SEQ ID NO:4:

| | | | | | | | | | | | | | | | | |
|---|---|---|---|---|---|---|---|---|---|---|---|---|---|---|---|---|
| ATG | ATG | AGT | AAA | TGT | AGT | TCT | CAT | AAT | AGT | CTG | TAT | GCA | CTG | ATA | TTG | 48 |
| Met | Met | Ser | Lys | Cys | Ser | Ser | His | Asn | Ser | Leu | Tyr | Ala | Leu | Ile | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| CTT | GCA | CAA | TAT | CAT | AAT | ATA | ACT | GTC | AAT | GCT | GAA | ACT | ATA | AGG | CAT | 96 |
| Leu | Ala | Gln | Tyr | His | Asn | Ile | Thr | Val | Asn | Ala | Glu | Thr | Ile | Arg | His | |
| | | | 20 | | | | | 25 | | | | | 30 | | | |

| | | | | | | | | | | | | | | | | |
|---|---|---|---|---|---|---|---|---|---|---|---|---|---|---|---|---|
| CAG | TAT | AAT | ACC | CAC | ACA | CAA | GAT | TTT | GGG | GTG | ACT | GAA | TGG | TTA | CTG | 144 |
| Gln | Tyr | Asn | Thr | His | Thr | Gln | Asp | Phe | Gly | Val | Thr | Glu | Trp | Leu | Leu | |
| | | 35 | | | | | 40 | | | | | 45 | | | | |

| | | | | | | | | | | | | | | | | |
|---|---|---|---|---|---|---|---|---|---|---|---|---|---|---|---|---|
| GCA | GCG | AAA | TCT | ATT | GGC | TTA | AAA | GCA | AAA | TAT | GTA | GAA | AAA | CAT | TTT | 192 |
| Ala | Ala | Lys | Ser | Ile | Gly | Leu | Lys | Ala | Lys | Tyr | Val | Glu | Lys | His | Phe | |
| | 50 | | | | | 55 | | | | | 60 | | | | | |

| | | | | | | | | | | | | | | | | |
|---|---|---|---|---|---|---|---|---|---|---|---|---|---|---|---|---|
| TCC | AGA | TTG | TCA | ATA | ATT | TCT | TTA | CCT | GCG | TTG | ATA | TGG | CGG | GAT | GAC | 240 |
| Ser | Arg | Leu | Ser | Ile | Ile | Ser | Leu | Pro | Ala | Leu | Ile | Trp | Arg | Asp | Asp | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| GGT | AAG | CAT | TAT | ATA | TTG | TCT | CGT | ATT | ACT | AAA | GAT | TCA | TCA | CGC | TAT | 288 |
| Gly | Lys | His | Tyr | Ile | Leu | Ser | Arg | Ile | Thr | Lys | Asp | Ser | Ser | Arg | Tyr | |
| | | | | 85 | | | | | 90 | | | | | 95 | | |

| | | | | | | | | | | | | | | | | |
|---|---|---|---|---|---|---|---|---|---|---|---|---|---|---|---|---|
| CTT | GTT | TAT | GAT | CCA | GAA | CAA | CAT | CAG | TCA | CTA | ACT | TTT | AGT | CGG | GAT | 336 |
| Leu | Val | Tyr | Asp | Pro | Glu | Gln | His | Gln | Ser | Leu | Thr | Phe | Ser | Arg | Asp | |
| | | | 100 | | | | | 105 | | | | | 110 | | | |

| | | | | | | | | | | | | | | | | |
|---|---|---|---|---|---|---|---|---|---|---|---|---|---|---|---|---|
| GAG | TTT | GAA | AAA | CTG | TAT | CAG | GGA | AAA | GTC | ATT | CTG | GTT | ACG | TCA | AGA | 384 |
| Glu | Phe | Glu | Lys | Leu | Tyr | Gln | Gly | Lys | Val | Ile | Leu | Val | Thr | Ser | Arg | |
| | | 115 | | | | | 120 | | | | | 125 | | | | |

| | | | | | | | | | | | | | | | | |
|---|---|---|---|---|---|---|---|---|---|---|---|---|---|---|---|---|
| GCA | ACA | GTA | GTC | GGA | GAG | TTA | GCT | AAA | TTT | GAT | TTT | TCT | TGG | TTT | ATC | 432 |
| Ala | Thr | Val | Val | Gly | Glu | Leu | Ala | Lys | Phe | Asp | Phe | Ser | Trp | Phe | Ile | |
| | 130 | | | | | 135 | | | | | 140 | | | | | |

| | | | | | | | | | | | | | | | | |
|---|---|---|---|---|---|---|---|---|---|---|---|---|---|---|---|---|
| CCC | TCT | GTT | GTG | AAA | TAC | AGG | AGG | ATT | TTA | CTT | GAG | GTG | TTA | ACT | GTT | 480 |
| Pro | Ser | Val | Val | Lys | Tyr | Arg | Arg | Ile | Leu | Leu | Glu | Val | Leu | Thr | Val | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| TCT | GCT | TTT | ATT | CAG | TTT | CTT | GCG | TTA | ATA | ACA | CCT | CTT | TTT | TTT | CAG | 528 |
| Ser | Ala | Phe | Ile | Gln | Phe | Leu | Ala | Leu | Ile | Thr | Pro | Leu | Phe | Phe | Gln | |
| | | | | 165 | | | | | 170 | | | | | 175 | | |

| | | | | | | | | | | | | | | | | |
|---|---|---|---|---|---|---|---|---|---|---|---|---|---|---|---|---|
| GTT | GTA | ATG | GAT | AAG | GTT | TTA | GTT | CAC | CGG | GGG | TTT | TCA | ACG | TTA | AAT | 576 |
| Val | Val | Met | Asp | Lys | Val | Leu | Val | His | Arg | Gly | Phe | Ser | Thr | Leu | Asn | |
| | | | 180 | | | | | 185 | | | | | 190 | | | |

| | | | | | | | | | | | | | | | | |
|---|---|---|---|---|---|---|---|---|---|---|---|---|---|---|---|---|
| ATT | ATC | ACA | ATA | GCA | TTT | ATT | ATA | GTG | ATA | CTT | TTT | GAA | GTG | ATA | TTA | 624 |
| Ile | Ile | Thr | Ile | Ala | Phe | Ile | Ile | Val | Ile | Leu | Phe | Glu | Val | Ile | Leu | |
| | | | 195 | | | | | 200 | | | | | 205 | | | |

| | | | | | | | | | | | | | | | | |
|---|---|---|---|---|---|---|---|---|---|---|---|---|---|---|---|---|
| ACC | GGA | GCC | AGA | ACT | TAT | ATT | TTC | TCT | CAT | ACT | ACA | AGT | CGT | ATT | GAC | 672 |
| Thr | Gly | Ala | Arg | Thr | Tyr | Ile | Phe | Ser | His | Thr | Thr | Ser | Arg | Ile | Asp | |
| | | 210 | | | | | 215 | | | | | 220 | | | | |

| | | | | | | | | | | | | | | | | |
|---|---|---|---|---|---|---|---|---|---|---|---|---|---|---|---|---|
| GTC | GAA | CTG | GGT | GCT | AAG | TTA | TTC | AGA | CAT | TTG | CTT | GCA | TTG | CCT | GTT | 720 |
| Val | Glu | Leu | Gly | Ala | Lys | Leu | Phe | Arg | His | Leu | Leu | Ala | Leu | Pro | Val | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| TCA | TAT | TTT | GAA | AAT | CGC | AGG | GTC | GGA | GAG | ACC | GTT | GCC | AGA | GTA | AGG | 768 |
| Ser | Tyr | Phe | Glu | Asn | Arg | Arg | Val | Gly | Glu | Thr | Val | Ala | Arg | Val | Arg | |
| | | | | 245 | | | | | 250 | | | | | 255 | | |

| | | | | | | | | | | | | | | | | |
|---|---|---|---|---|---|---|---|---|---|---|---|---|---|---|---|---|
| GAA | CTG | GAG | CAA | ATT | CGT | AAT | TTT | TTA | ACC | GGA | CAA | GCG | TTG | ACA | TCA | 816 |
| Glu | Leu | Glu | Gln | Ile | Arg | Asn | Phe | Leu | Thr | Gly | Gln | Ala | Leu | Thr | Ser | |
| | | | 260 | | | | | 265 | | | | | 270 | | | |

| | | | | | | | | | | | | | | | | |
|---|---|---|---|---|---|---|---|---|---|---|---|---|---|---|---|---|
| GTT | CTT | GAT | CTA | TTT | TTT | TCT | GTA | ATA | TTT | TTT | TGT | GTC | ATG | TGG | TAT | 864 |
| Val | Leu | Asp | Leu | Phe | Phe | Ser | Val | Ile | Phe | Phe | Cys | Val | Met | Trp | Tyr | |
| | | 275 | | | | | 280 | | | | | 285 | | | | |

| | | | | | | | | | | | | | | | | |
|---|---|---|---|---|---|---|---|---|---|---|---|---|---|---|---|---|
| TAC | AGC | CCT | CAA | TTA | ACA | CTG | GTT | ATA | TTA | TTG | TCA | CTA | CCT | TGT | TAT | 912 |
| Tyr | Ser | Pro | Gln | Leu | Thr | Leu | Val | Ile | Leu | Leu | Ser | Leu | Pro | Cys | Tyr | |
| | 290 | | | | | 295 | | | | | 300 | | | | | |

```
GTT  ATA  TGG  TCA  TTG  TTT  ATA  TCA  CCC  TTA  TTA  CGT  CGA  CGT  CTT  GAT      960
Val  Ile  Trp  Ser  Leu  Phe  Ile  Ser  Pro  Leu  Leu  Arg  Arg  Arg  Leu  Asp
305            310                      315                           320

GAT  AAG  TTT  CTC  AGG  AAT  GCA  GAA  AAT  CAA  GCT  T                           994
Asp  Lys  Phe  Leu  Arg  Asn  Ala  Glu  Asn  Gln  Ala
                    325                 330
```

( 2 ) INFORMATION FOR SEQ ID NO:5:

( i ) SEQUENCE CHARACTERISTICS:
        ( A ) LENGTH: 331 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met  Met  Ser  Lys  Cys  Ser  Ser  His  Asn  Ser  Leu  Tyr  Ala  Leu  Ile  Leu
  1              5                   10                        15

Leu  Ala  Gln  Tyr  His  Asn  Ile  Thr  Val  Asn  Ala  Glu  Thr  Ile  Arg  His
               20                  25                        30

Gln  Tyr  Asn  Thr  His  Thr  Gln  Asp  Phe  Gly  Val  Thr  Glu  Trp  Leu  Leu
          35                  40                       45

Ala  Ala  Lys  Ser  Ile  Gly  Leu  Lys  Ala  Lys  Tyr  Val  Glu  Lys  His  Phe
     50                  55                       60

Ser  Arg  Leu  Ser  Ile  Ile  Ser  Leu  Pro  Ala  Leu  Ile  Trp  Arg  Asp  Asp
 65                 70                      75                            80

Gly  Lys  His  Tyr  Ile  Leu  Ser  Arg  Ile  Thr  Lys  Asp  Ser  Ser  Arg  Tyr
                    85                  90                        95

Leu  Val  Tyr  Asp  Pro  Glu  Gln  His  Gln  Ser  Leu  Thr  Phe  Ser  Arg  Asp
               100                 105                       110

Glu  Phe  Glu  Lys  Leu  Tyr  Gln  Gly  Lys  Val  Ile  Leu  Val  Thr  Ser  Arg
          115                 120                      125

Ala  Thr  Val  Val  Gly  Glu  Leu  Ala  Lys  Phe  Asp  Phe  Ser  Trp  Phe  Ile
     130                 135                      140

Pro  Ser  Val  Val  Lys  Tyr  Arg  Arg  Ile  Leu  Leu  Glu  Val  Leu  Thr  Val
145                 150                      155                          160

Ser  Ala  Phe  Ile  Gln  Phe  Leu  Ala  Leu  Ile  Thr  Pro  Leu  Phe  Phe  Gln
                    165                 170                       175

Val  Val  Met  Asp  Lys  Val  Leu  Val  His  Arg  Gly  Phe  Ser  Thr  Leu  Asn
               180                 185                       190

Ile  Ile  Thr  Ile  Ala  Phe  Ile  Ile  Val  Ile  Leu  Phe  Glu  Val  Ile  Leu
          195                 200                      205

Thr  Gly  Ala  Arg  Thr  Tyr  Ile  Phe  Ser  His  Thr  Thr  Ser  Arg  Ile  Asp
     210                 215                      220

Val  Glu  Leu  Gly  Ala  Lys  Leu  Phe  Arg  His  Leu  Leu  Ala  Leu  Pro  Val
225                 230                      235                          240

Ser  Tyr  Phe  Glu  Asn  Arg  Arg  Val  Gly  Glu  Thr  Val  Ala  Arg  Val  Arg
                    245                 250                       255

Glu  Leu  Glu  Gln  Ile  Arg  Asn  Phe  Leu  Thr  Gly  Gln  Ala  Leu  Thr  Ser
               260                 265                       270

Val  Leu  Asp  Leu  Phe  Phe  Ser  Val  Ile  Phe  Phe  Cys  Val  Met  Trp  Tyr
          275                 280                      285

Tyr  Ser  Pro  Gln  Leu  Thr  Leu  Val  Ile  Leu  Leu  Ser  Leu  Pro  Cys  Tyr
     290                 295                      300

Val  Ile  Trp  Ser  Leu  Phe  Ile  Ser  Pro  Leu  Leu  Arg  Arg  Arg  Leu  Asp
```

```
305                    310                    315                    320
Asp Lys Phe Leu Arg Asn Ala Glu Asn Gln Ala
                    325                    330
```

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i x ) FEATURE:
        ( A ) NAME/KEY: misc_feature
        ( B ) LOCATION: 1..21
        ( D ) OTHER INFORMATION: /standard_name="Target region for
            the RH 26 probe."

( x i ) SEQUENCE DESCRIPTION: SEQ ID NO:6:

```
CTGTTTCCCA GAATAAAGCT T                                                    21
```

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i x ) FEATURE:
        ( A ) NAME/KEY: misc_feature
        ( B ) LOCATION: 1..21
        ( D ) OTHER INFORMATION: /standard_name="Target region for
            the RH 27 probe."

( x i ) SEQUENCE DESCRIPTION: SEQ ID NO:7:

```
AGTCTGTCAA CAGCAATTTC A                                                    21
```

( 2 ) INFORMATION FOR SEQ ID NO:8:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i x ) FEATURE:
        ( A ) NAME/KEY: misc_feature
        ( B ) LOCATION: 1..23
        ( D ) OTHER INFORMATION: /standard_name="Target region for
            the RH 28 probe."

( x i ) SEQUENCE DESCRIPTION: SEQ ID NO:8:

```
CAGAATATTA TAAGCTCCGT GTG                                                  23
```

( 2 ) INFORMATION FOR SEQ ID NO:9:

( i ) SEQUENCE CHARACTERISTICS:
        ( A ) LENGTH: 21 base pairs ( B ) TYPE: nucleic acid
            ( C ) STRANDEDNESS: single
            ( D ) TOPOLOGY: linear ( i i ) MOLECULE TYPE: DNA ( i i i ) HYPOTHETICAL: NO ( i x ) FEATURE:
            ( A ) NAME/KEY: misc_feature
            ( B ) LOCATION: 1..21
            ( D ) OTHER INFORMATION: /standard_name="Target region for
                  the RH 29 probe."

( x i ) SEQUENCE DESCRIPTION: SEQ ID NO:9:

GACATCATTT GACTCATTAA A                                                                                   21

( 2 ) INFORMATION FOR SEQ ID NO:10:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: DNA ( i i i ) HYPOTHETICAL: NO ( i x ) FEATURE:
            ( A ) NAME/KEY: misc_feature
            ( B ) LOCATION: 1..21
            ( D ) OTHER INFORMATION: /standard_name="Target region for
                  the RH 30 probe."

( x i ) SEQUENCE DESCRIPTION: SEQ ID NO:10:

TTTAATGAGT CAAATGATGT C                                                                                   21

( 2 ) INFORMATION FOR SEQ ID NO:11:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: DNA ( i i i ) HYPOTHETICAL: NO ( i x ) FEATURE:
            ( A ) NAME/KEY: misc_feature
            ( B ) LOCATION: 1..21
            ( D ) OTHER INFORMATION: /standard_name="Target region for
                  the RH 31 probe"

( x i ) SEQUENCE DESCRIPTION: SEQ ID NO:11:

CAAATGATGT CAATGGGATA A                                                                                   21

( 2 ) INFORMATION FOR SEQ ID NO:12:

( i ) SEQUENCE CHARACTERISTICS:
            ( A ) LENGTH: 26 base pairs
            ( B ) TYPE: nucleic acid
            ( C ) STRANDEDNESS: single
            ( D ) TOPOLOGY: linear ( i i ) MOLECULE TYPE: DNA ( i i i ) HYPOTHETICAL: NO ( i x ) FEATURE:
            ( A ) NAME/KEY: misc_feature 5,475,098

-continued ( B ) LOCATION: 1..26
      ( D ) OTHER INFORMATION: /standard_name="Target region for
          the RH 35 probe."

( x i ) SEQUENCE DESCRIPTION: SEQ ID NO:12:

TGACAGAATA TTATAAGCTC CGTGTG          26

( 2 ) INFORMATION FOR SEQ ID NO:13:

( i ) SEQUENCE CHARACTERISTICS:
      ( A ) LENGTH: 28 base pairs
      ( B ) TYPE: nucleic acid
      ( C ) STRANDEDNESS: single
      ( D ) TOPOLOGY: linear ( i i ) MOLECULE TYPE: DNA ( i i i ) HYPOTHETICAL: NO ( i x ) FEATURE:
      ( A ) NAME/KEY: misc_feature
      ( B ) LOCATION: 1..28
      ( D ) OTHER INFORMATION: /standard_name="Target region for
          the RH 36 probe."

( x i ) SEQUENCE DESCRIPTION: SEQ ID NO:13:

TCATTTAATG AGTCAAATGA TGTCAATG          28

( 2 ) INFORMATION FOR SEQ ID NO:14:

( i ) SEQUENCE CHARACTERISTICS:
      ( A ) LENGTH: 28 base pairs
      ( B ) TYPE: nucleic acid
      ( C ) STRANDEDNESS: single
      ( D ) TOPOLOGY: linear ( i i ) MOLECULE TYPE: DNA ( i i i ) HYPOTHETICAL: NO ( i x ) FEATURE:
      ( A ) NAME/KEY: misc_feature
      ( B ) LOCATION: 1..28
      ( D ) OTHER INFORMATION: /standard_name="Target region for
          the RH 37 probe."

( x i ) SEQUENCE DESCRIPTION: SEQ ID NO:14:

AGTCAAATGA TGTCAATGGG ATAACATT          28

( 2 ) INFORMATION FOR SEQ ID NO:15:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA ( i i i ) HYPOTHETICAL: NO ( i x ) FEATURE:
      ( A ) NAME/KEY: misc_feature
      ( B ) LOCATION: 1..21
      ( D ) OTHER INFORMATION: /standard_name="RH 26 probe."

( x i ) SEQUENCE DESCRIPTION: SEQ ID NO:15:

AAGCTTTATT CTGGGAAACA G          21

( 2 ) INFORMATION FOR SEQ ID NO:16:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: DNA ( i i i ) HYPOTHETICAL: NO ( i x ) FEATURE:
            ( A ) NAME/KEY: misc_feature
            ( B ) LOCATION: 1..21
            ( D ) OTHER INFORMATION: /standard_name="RH 27 probe."

( x i ) SEQUENCE DESCRIPTION: SEQ ID NO:16:

TGAAATTGCT GTTGACAGAC T                            21

( 2 ) INFORMATION FOR SEQ ID NO:17:

( i ) SEQUENCE CHARACTERISTICS:
            ( A ) LENGTH: 23 base pairs
            ( B ) TYPE: nucleic acid
            ( C ) STRANDEDNESS: single
            ( D ) TOPOLOGY: linear ( i i ) MOLECULE TYPE: DNA ( i i i ) HYPOTHETICAL: NO ( i x ) FEATURE:
            ( A ) NAME/KEY: misc_feature
            ( B ) LOCATION: 1..23
            ( D ) OTHER INFORMATION: /standard_name="RH 28 probe."

( x i ) SEQUENCE DESCRIPTION: SEQ ID NO:17:

CACACGGAGC TTATAATATT CTG                          23

( 2 ) INFORMATION FOR SEQ ID NO:18:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: DNA ( i i i ) HYPOTHETICAL: NO ( i x ) FEATURE:
            ( A ) NAME/KEY: misc_feature
            ( B ) LOCATION: 1..21
            ( D ) OTHER INFORMATION: /standard_name="RH 29 probe."

( x i ) SEQUENCE DESCRIPTION: SEQ ID NO:18:

TTTAATGAGT CAAATGATGT C                            21

( 2 ) INFORMATION FOR SEQ ID NO:19:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: DNA ( i i i ) HYPOTHETICAL: NO ( i x ) FEATURE:
            ( A ) NAME/KEY: misc_feature
            ( B ) LOCATION: 1..21

(D) OTHER INFORMATION: /standard_name="RH 30 probe."

(x i) SEQUENCE DESCRIPTION: SEQ ID NO:19:

GACATCATTT GACTCATTAA A 21

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iii) HYPOTHETICAL: NO (ix) FEATURE:
        (A) NAME/KEY: misc_feature
        (B) LOCATION: 1..21
        (D) OTHER INFORMATION: /standard_name="RH 31 probe."

(xi) SEQUENCE DESCRIPTION: SEQ ID NO:20:

TTATCCCATT GACATCATTT G 21

(2) INFORMATION FOR SEQ ID NO:21:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (iii) HYPOTHETICAL: NO (ix) FEATURE:
        (A) NAME/KEY: misc_feature
        (B) LOCATION: 1..26
        (D) OTHER INFORMATION: /standard_name="RH 35 probe."

(xi) SEQUENCE DESCRIPTION: SEQ ID NO:21:

CACACGGAGC TTATAATATT CTGTCA 26

(2) INFORMATION FOR SEQ ID NO:22:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (iii) HYPOTHETICAL: NO (ix) FEATURE:
        (A) NAME/KEY: misc_feature
        (B) LOCATION: 1..28
        (D) OTHER INFORMATION: /standard_name="RH 36 probe."

(xi) SEQUENCE DESCRIPTION: SEQ ID NO:22:

CATTGACATC ATTTGACTCA TTAAATGA 28

(2) INFORMATION FOR SEQ ID NO:23:

(i) SEQUENCE CHARACTERISTICS:
        (A) LENGTH: 28 base pairs
        (B) TYPE: nucleic acid
        (C) STRANDEDNESS: single ( D ) TOPOLOGY: linear ( i i ) MOLECULE TYPE: DNA ( i i i ) HYPOTHETICAL: NO ( i x ) FEATURE:
    ( A ) NAME/KEY: misc_feature
    ( B ) LOCATION: 1..28
    ( D ) OTHER INFORMATION: /standard_name="RH 37 probe."

( x i ) SEQUENCE DESCRIPTION: SEQ ID NO:23:

AATGTTATCC CATTGACATC ATTTGACT      28

( 2 ) INFORMATION FOR SEQ ID NO:24:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i x ) FEATURE:
    ( A ) NAME/KEY: misc_feature
    ( B ) LOCATION: 1..22
    ( D ) OTHER INFORMATION: /standard_name="Target region for
        the RH 32 probe."

( x i ) SEQUENCE DESCRIPTION: SEQ ID NO:24:

GAGAACTACA TTTACTCATC AT      22

( 2 ) INFORMATION FOR SEQ ID NO:25:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i x ) FEATURE:
    ( A ) NAME/KEY: misc_feature
    ( B ) LOCATION: 1..22
    ( D ) OTHER INFORMATION: /standard_name="Target region for
        the RH 33 probe."

( x i ) SEQUENCE DESCRIPTION: SEQ ID NO:25:

CTTCTGGTTA CGTCAAGAGC AA      22

( 2 ) INFORMATION FOR SEQ ID NO:26:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i x ) FEATURE:
    ( A ) NAME/KEY: misc_feature
    ( B ) LOCATION: 1..22
    ( D ) OTHER INFORMATION: /standard_name="RH 32 probe."

( x i ) SEQUENCE DESCRIPTION: SEQ ID NO:26:

ATGATGAGTA AATGTAGTTC TC                        22

( 2 ) INFORMATION FOR SEQ ID NO:27:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i x ) FEATURE:
    ( A ) NAME/KEY: misc_feature
    ( B ) LOCATION: 1..22
    ( D ) OTHER INFORMATION: /standard_name="RH 33 probe."

( x i ) SEQUENCE DESCRIPTION: SEQ ID NO:27:

TTGCTCTTGA CGTAACCAGA AG                        22

( 2 ) INFORMATION FOR SEQ ID NO:28:

( i ) SEQUENCE CHARACTERISTICS:
    ( A ) LENGTH: 49 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i x ) FEATURE:
    ( A ) NAME/KEY: misc_feature
    ( B ) LOCATION: 1..49
    ( D ) OTHER INFORMATION: /standard_name="Target region for
          the RH Intergenic Region Probe."

( x i ) SEQUENCE DESCRIPTION: SEQ ID NO:28:

ATAACGATGA CCATTCCTCC TGGAATGGCC ATCACCTCCT CTTTTAGTC            49

( 2 ) INFORMATION FOR SEQ ID NO:29:

( i ) SEQUENCE CHARACTERISTICS:
    ( A ) LENGTH: 49 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i x ) FEATURE:
    ( A ) NAME/KEY: misc_feature
    ( B ) LOCATION: 1..49
    ( D ) OTHER INFORMATION: /standard_name="RH Intergenic
          Region Probe."

( x i ) SEQUENCE DESCRIPTION: SEQ ID NO:29:

GACTAAAAGA GGAGGTGATG GCCATTCCAG GAGGAATGGT CATCGTTAT            49

DISTINCTIVE DNA SEQUENCE OF E. COLI 0157:H7 AND ITS USE FOR THE RAPID, SENSITIVE AND SPECIFIC DETECTION OF 0157:H7 AND OTHER ENTEROHEMORRHAGIC E. COLI

FIELD OF THE INVENTION

The present invention relates, in general, to an hlyA gene, an hlyB gene and an intergenic region between the hlyA gene and the hlyB gene which are present in enterohemorrhagic E. coli. More particularly, the present invention relates to methods for detecting enterohemorrhagic E. coli by targeting the hlyA gene, the hlyB gene, the intergenic region between the hlyA and the hlyB genes, combinations thereof or, fragments thereof. Such methods rely on nucleic acid probes and amplification primers specific for subsequences of the hlyA gene, the hlyB gene, the intergenic region between the hlyA and the hlyB genes, combination thereof or, fragments thereof.

BACKGROUND OF THE INVENTION

Enterohemorrhagic Escherichia coli (EHEC) are now recognized as the causative agents of enterohemorrhagic colitis (EC), hemolytic uremic syndrome (HUS) and mesenteric adenitis (MA). Enterohemorrhagic colitis is characterized by severe, crampy abdominal pain, initially watery diarrhea followed by copious, bloody diarrhea, with little or no fever; hemolytic uremic syndrome is one of the complications resulting from enterohemorrhagic colitis. Enterohemorrhagic colitis occurs most frequently in developed countries, and most outbreaks of this disease have been associated with the consumption of contaminated meats (e.g., undercooked ground beef) and dairy products (e.g., raw milk). Escherichia coli serotype O157:H7 is the most frequent EHEC isolate, but many other serotypes of E. coli that are capable of causing equally devastating foodborne outbreaks of EC and HUS have been identified. Presently, the EHECs and, in particular, E. coli O157:H7 are among the most serious bacterial pathogens confronting the public health and food safety agencies.

To date, however, there is no known single genetic marker for virulent EHEC strains which can be used to detect not only O157:H7, but all serogroups of EHEC. Current immunological assays based on the O157:H7 serogroup generate false negatives due to the existence of many non-O157:H7 serogroups of EHEC. Moreover, immunological assays require a lengthy microbiological work-up and, thus, are expensive and time-consuming. In contrast to immunological assays, current rapid, genetic methods target the genes that encode the shiga-like toxins I and II (i.e., slt-I and slt-II respectively) and a particular allele of uidA. The presence of these genes is broadly associated with EHEC, but no real correlation with virulence can be established.

In fact, there are known EHECs positive for both slt-I and slt-II, but there are also known EHECs that are negative for both slt-I and slt-II or, that are positive for only one slt. Moreover, many bacteria possess slt-I and/or slt-II genes without being associated with EHEC, HUS or EC. Enteropathogenic E. coli (EPEC), for example, is slt-positive, but causes only mild, persistent diarrhea. In addition, an entire new class of diarrheagenic E. coli, known as entero-SLT-producing and invasive E. coli (ESIEC), has been identified that is positive for sit. Of 54 strains belonging to ESIEC, 53 were slt-I positive and 3 were slt-II positive. Furthermore, Shigella dysenteriae type I possesses slt-I, but causes a very different disease. As such, slt probes detect entire classes of bacteria irrelevant to EHEC and, thus, the presence of slt-I and/or slt-II genes is not an adequate indicator of EHEC risk.

Further, the uidA allele identifies many O157:H7 strains of EHEC. It is recognized, however, that uidA does not encode a real virulence factor. The uidA gene is not expressed in EHEC because the allele characteristic of O157:H7 is not an open reading frame and, thus, it is unable to express a protein. It is believed that this allele is most probably a residual trait of the ancestral EHEC from which the O157:H7 serogroup clone evolved. In addition, the uidA gene is not real useful as a target because it does not detect non-O157:H7 EHEC strains. Although E. coli O157:H7 is the major serogroup of EHEC, other serogroups of E. coli which can cause EC and HUS cannot be ignored. E. coli strains O157:H45, O157:H19, O26: H11, O22:H8, O55:H6, O11:H8, O11:H- and O145:NM, for example, are also isolated from victims of EC and HUS. Moreover, it is likely that more E. coli serotypes will be identified as EHEC agents when the genetic mechanisms underlying the pathogenesis of this organism is more fully understood.

From the foregoing, it is apparent that the immunological assays presently being used to detect EHECs fail to detect non-O157:H7 EHECs and, in addition, they are labor-intensive and time-consuming. Moreover, the rapid, genetic assays being used are founded on known genes that do not correlate well with EHEC and, thus, they are prone to false positives and false negatives. False positives result from the relatively harmless slt-bearing bacteria; false negatives result from the many EHEC strains lacking slt-I, slt-II and uidA, all of which can cause devastating EC and HUS. As such, there still remains a need in the art for rapid, sensitive and highly specific methods for the detection of enterohemorrhagic E. coli and, in particular, O157:H7 E. coli. The present invention remedies this need by providing such methods.

SUMMARY OF THE INVENTION

It has now been discovered that an hlyA gene, an hlyB gene and an intergenic region between the hlyA and hlyB genes are present in enterohemorrhagic E. coli associated with enterohemorrhagic colitis (EC), hemolytic uremic syndrome (HUS) and mesenteric adenitis (MA), but absent in bacteria not associated with such diseases. It has further been discovered that the hlyA gene, the hlyB gene and the intergenic region between the hlyA and hlyB genes can be used as targets for the specific detection of enterohemorrhagic E. coli bacterial pathogens and, in particular, O157:H7 E. coli.

The hlyA and hlyB genes present in EHECs are novel, but they bear some resemblance to the hlyA and hlyB genes of several pathogens, namely E. coli from a urinary tract infection, Proteus vulgaris, Actinobacillus suis, A. pleuropneumoniae and Pasturella haemolytica. The homology at the DNA level, however, is a relatively low 70% for the closest relation to the EHEC variant of hlyA, and a relatively low 73% for the closest relation to the EHEC variant of hlyB. It is presently thought that the hlyA and hlyB genes are the virulence factors responsible for the unique pathogenesis of EHEC. In fact, a direct correlation has been found to exist between the presence of the hlyA and hlyB genes and the disease symptoms of EC, HUS and MA, regardless of serogroup, slt-I, slt-II or uidA type or, O157:H7 serogroup. As such, the hlyA gene, the hlyB gene and the intergenic region between the hlyA and hlyB genes can be used as The phrase "nucleic acid sequence" refers to a single- or double-stranded polymer of deoxyribonucleotide or ribonucleotide bases read from the 5' to the 3' end. It includes both self-replicating plasmids, infectious polymers of DNA or RNA and nonfunctional DNA or RNA. Moreover, the nucleic acid sequences set forth herein are the sense strands. It will be readily apparent to those in the art that the antisense strands, i.e., the strands complementary to the sense strands, are also included within the scope of the present invention. Additionally, substantial nucleic acid sequence identity exists when a nucleic acid segment will hybridize, under selective hybridization conditions, to a complement of another nucleic acid strand. Nucleotide sizes are given in either kilobases (kb) or base pairs (bp). These are estimates derived from agarose or acrylamide gel electrophoresis.

The phrase "DNA sequence" refers to a single- or double-stranded DNA polymer composed of the nucleotide bases, adenosine, thymidine, cytosine and guanosine.

The phrase "nucleic acid sequence encoding" refers to a nucleic acid sequence which directs the expression of a specific protein or peptide. The nucleic acid sequences include both the DNA sequence that is transcribed into RNA and the RNA sequence that is translated into the protein. The nucleic acid sequence includes both the full length nucleic acid sequence as well as non-full length sequences derived from the full length sequence. It will be understood by those of skill that the sequence includes the degenerate codons of the native sequence or, sequences which may be introduced to provide codon preference in a specific host cell.

The term "complementary" refers to a nucleic acid segment that will hybridize, under selective hybridization conditions, to a complement of another nucleic acid strand. Selectivity of hybridization exists when hybridization occurs that is more selective than total lack of specificity. Typically, selective hybridization will occur when there is at least about 55% identity over a stretch of at least 14–25 nucleotides, preferably at least about 65%, more preferably at least about 75%, and most preferably at least about 90%. See, Kanehisa, *Nucleic Acids Res.* 12:203 (1984), incorporated herein by reference.

"Isolated" or "substantially pure," when referring to nucleic acids, refer to those that have been purified away from other cellular components and contaminants, i.e., other cellular nucleic acids and/or proteins, by standard techniques, including, for example, alkaline/SDS treatment, CsCl banding, column chromatography, and others purification techniques well known in the art. See, e.g., *Methods in Enzymology*, Vol. 152: *Guide to Molecular Cloning Techniques* (Berger and Kimmel (eds.), San Diego: Academic Press, Inc. (1987)), and *Current Protocols in Molecular Biology* (Ausubel, et al., (ed.), Greene Publishing and Wiley-Interscience, New York (1987)), both of which are incorporated herein by reference.

"Nucleic acid probe" or "probe" refers to an oligonucleotide which binds through complementary base pairing to a subsequence of a target nucleic acid. The nucleic acid probe may be, for example, a DNA fragment prepared by amplification methods such as by PCR or, it may be synthesized by either the phosphoramidite method described by Beaucage and Carruthers (*Tetrahedron Lett.* 22:1859–1862 (1981)), or by the triester method according to Matteucci, et al. (*J. Am. Chem. Soc.* 103:3185 (1981)), both of which are incorporated herein by reference. A double stranded fragment may then be obtained, if desired, by annealing the chemically synthesized single strands together under appropriate conditions or, by synthesizing the complementary strand using DNA polymerase with an appropriate primer sequence. The probes are preferably directly labeled with, for example, radioisotopes or, indirectly labeled with, for example, biotin to which a streptavidin complex may later bind. Where a specific nucleic acid sequence is given, it is understood that the complementary strand is also identified and included as the complementary strand will work equally well in situations where the target is a double stranded nucleic acid.

A nucleic acid probe is complementary to a target nucleic acid when it will anneal only to a single desired position on that target nucleic acid under conditions determined as described below. Proper annealing conditions depend, for example, upon a probe's length, base composition, and the number of mismatches and their position on the probe, and must often be determined empirically. It will be understood by those of skill that minor mismatches can be accommodated by reducing the stringency of the hybridization media. For discussions of nucleic acid probe design and annealing conditions, see, e.g., Sambrook, et al., *Molecular Cloning: A Laboratory Manual* (2nd Ed., Vols. 1–3, Cold Spring Harbor Laboratory (1989)), *Methods in Enzymology*, Vol. 152: *Guide to Molecular Cloning Techniques* (Berger and Kimmel (eds.), San Diego: Academic Press, Inc. (1987)), or *Current Protocols in Molecular Biology*, (Ausubel, et al. (eds.), Greene Publishing and Wiley-Interscience, New York (1987), all of which are incorporated herein by reference.

"Amplification reaction mixture" refers to an aqueous solution comprising the various reagents used to amplify a target nucleic acid. These include, but are not limited to, the following: enzymes, aqueous buffers, salts, target nucleic acid, and nucleoside triphosphates. Depending upon the context, the mixture can be either a complete or incomplete amplification reaction mixture.

"Amplification reaction system" refers to any in vitro means for multiplying the copies of a target sequence of nucleic acid. Such methods include, but are not limited to, polymerase chain reaction amplification (i.e., PCR), DNA ligase, QB RNA replicase, and RNA transcription-based amplification systems. These reaction systems involve multiple amplification reagents and are more fully described hereinbelow.

"Amplification reaction tube(s)" refers to a container suitable for holding the amplification reagents. Generally, the tube is constructed of inert components so as not to inhibit or interfere with the amplification reaction system being used. When the reaction system requires thermal cycling of repeated heating and cooling, the tube must be able to withstand the cycling process and must precisely fit the wells of the thermocycler.

"Amplification reagents" refer to the various buffers, enzymes, primers, nucleoside triphosphates (both conventional and unconventional), and probes used to perform the selected amplification procedure.

"Amplifying" or "Amplification", which typically refers to an "exponential" increase in target nucleic acid, is being used herein to describe both linear and exponential increases in the number of a select target sequence of nucleic acid.

"Bind(s) substantially" refers to complementary hybridization between oligonucleotides and embraces minor mismatches which can be accommodated by reducing the stringency of the hybridization media to achieve the desired priming of the PCR polymerases.

"Hybridizing" refers the binding of two single stranded nucleic acids via complementary base pairing.

"Nucleotide polymerases" refers to enzymes that are capable of catalyzing the synthesis of DNA or RNA from nucleoside triphosphate precursors. In the amplification reactions of this invention, the polymerases are template dependent and typically extend from the 3' end of the polymer being formed. In a presently preferred embodiment, the polymerase is thermostable as described in U.S. Pat. No. 4,889,819.

"Primer" or "nucleic acid polymerase primer(s)" refers to an oligonucleotide, whether natural or synthetic, capable of acting as a point of initiation of DNA synthesis under conditions in which synthesis of a primer extension product complementary to a nucleic acid strand is initiated, i.e., in the presence of four different nucleotide triphosphates and an agent for polymerization (e.g., DNA polymerase or reverse transcriptase) in an appropriate buffer and at a suitable temperature. A primer is preferably an oligodeoxyribonucleotide and is single stranded for maximum efficiency in amplification, but may also be double stranded. If double stranded, the primer is first treated to separate its strands before being used to prepare extension products. The exact length of a primer will depend on many factors, but typically ranges from 15 to 30 nucleotides. Short primer molecules generally require cooler temperatures to form sufficiently stable hybrid complexes with the template. A primer need not reflect the exact sequence of the template, but must be sufficiently complementary to hybridize with a template. An example of a non-complementary sequence which may be incorporated into the primer is a sequence which encodes a restriction enzyme recognition site (see, e.g., U.S. Pat. No. 4,800,159). Moreover, where a specific nucleic acid sequence is given, it is understood that the complementary strand is also identified and included as the complementary strand will work equally well in situations where the target is a double stranded nucleic acid.

A primer can be labeled, if desired, by incorporating a label detectable by spectroscopic, photochemical, biochemical, immunochemical or, chemical means. Suitable labels include, for example, $^{32}P$, fluorescent dyes, electron-dense reagents, enzymes (as commonly used in ELISAS), biotin or, haptens or proteins for which antisera or monoclonal antibodies are available. A label can also be used to "capture" the primer so as to facilitate the immobilization of either the primer or amplified DNA on a solid support.

"Recombinant" when referring to a nucleic acid probe refers to an oligonucleotide which is free of native proteins and nucleic acid typically associated with probes isolated from the cell which naturally contains the probe sequence as a part of its native genome. Recombinant probes include those made by amplification means such as PCR and genetic cloning methods where bacteria are transformed with the recombinant probe.

"Subsequence" refers to a sequence of nucleic acids which comprise a part of a longer sequence of nucleic acids.

"Target region" refers to a subsequence of a nucleic acid which is to be analyzed, which usually contains polymorphic DNA sequences.

The phrases "expression control sequence" or "expression control cassette" refer to nucleotide sequences which are capable of affecting expression of a structural gene in a host compatible with such sequences. Such cassettes include at least a promoter and, optionally, transcription termination signals. The term "promoter" refers to a region of DNA upstream from the structural gene and involved in the recognition and binding of a DNA polymerase and other proteins necessary to initiate transcription. Additional factors necessary or helpful in effecting expression may also be used as described herein.

The term "operably linked" refers to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein ceding regions, contiguous and in the same reading frame.

Techniques for nucleic acid manipulation, such as subcloning nucleic acid sequences encoding polypeptides into expression vectors, labelling probes, DNA hybridization, and so on are described generally, for example, in Sambrook, et al. (1989) supra., Berger and Kimmel, (1987), supra. or Ausubel, et al., (1987), supra., both of which are incorporated herein by reference.

"Expression vectors," "cloning vectors" or "vectors" are often plasmids or other nucleic acid molecules that are able to replicate in a chosen host cell. Expression vectors may replicate autonomously, or they may replicate by being inserted into the genome of the host cell using methods well known in the art. Vectors that replicate autonomously will have an origin of replication or autonomous replicating sequence (ARS) that is functional in the chosen host cell(s). Often, it is desirable for a vector to be usable in more than one host cell, e.g., in E. coli for cloning and construction and in a mammalian cell for expression.

The term "plasmid" refers to an autonomous self-replicating circular DNA molecule and includes both the expression and nonexpression types. Where a recombinant microorganism or cell culture is described as hosting an "expression plasmid," this includes both extrachromosomal circular DNA molecules and DNA that has been incorporated into the host chromosome(s). Where a plasmid is being maintained by a host cell, the plasmid is either being stably replicated by the cells during mitosis as an autonomous structure or is incorporated within the host's genome.

The phrase "selectively hybridizing to" refers to a nucleic acid that hybridizes duplexes or binds only to DNA sequences encoding one protein or portions thereof when the DNA sequences encoding the protein are present in a cDNA library. A DNA sequence which selectively hybridizes to a given target sequence can include sequences which are shorter or longer than the target sequence so long as they meet the functional test set forth. Hybridization conditions are specified herein along with the source of the cDNA library. Typically, the hybridization is done in a Southern blot protocol using a 0.2×SSC, 0.1% SDS, 65° C. wash.

The term "SSC" refers to a citrate-saline solution of 0.15M sodium chloride and 15 mM sodium citrate (pH 7.0). Solutions are often expressed as multiples or fractions of this concentration. For example, 6×SSC refers to a solution having a sodium chloride and sodium citrate concentration of 6 times this amount or 0.9M sodium chloride and 90 mM sodium citrate. 0.2×SSC refers to a solution 0.2 times the SSC concentration or 0.03M sodium chloride and 3 mM sodium titrate.

The term "sample" as used herein refers to food, clinical and environmental samples suspected of containing enterohemorrhagic E. coli. Clinical samples include, but are not limited to, the following: stools, biopsies, explants, and other sources of tissue and bodily fluids. Food samples include, but are not limited to, the following: meats, dairy products, beverages, fruits and vegetables, all of which may be cooked, partially cooked or uncooked.

As used herein, "immunoglobulin" refers to molecules which have specific immunoreactive activity. Antibodies are typically tetramers of immunoglobulin molecules. As used herein, the term "antibody" refers to a protein consisting of one or more polypeptides substantially encoded by immunoglobulin genes. Immunoglobulin genes include those coding for the light chains, which may be of the kappa or lambda types, and those coding for the heavy chains, Heavy chain types are alpha, gamma, delta, epsilon and mu. The carboxy terminal portions of immunoglobulin heavy and light chains are constant regions, while the amino terminal portions are encoded by the myriad of immunoglobulin variable region genes. The variable regions of an immunoglobulin are the portions that provide antigen recognition specificity. The immunoglobulins may exist in a variety of forms including, for example, Fv, Fab, and F(ab)$_2$, as well as in single chains (See, e.g., Huston, et al., *Proc. Nat. Acad. Sci. U.S.A.*, 85:5879–5883 (1988) and Bird, et al., *Science* 242:423–426 (1988), which are incorporated herein by reference). (See generally, Hood, et al., "Immunology," (Benjamin, N.Y., 2nd ed. (1984)), and Hunkapiller and Hood, *Nature* 323:15–16 (1986), which are incorporated herein by reference). Single-chain antibodies, in which genes for a heavy chain and a light chain are combined into a single coding sequence, may also be used.

"Monoclonal antibodies" may be obtained by various techniques familiar to those skilled in the art. Briefly, spleen cells from an animal immunized with a desired antigen are immortalized, commonly by fusion with a myeloma cell. (See, e.g., Kohler and Milstein, *Eur. J. Immunol.* 6:511–519 (1976), incorporated herein by reference). Alternative methods of immortalization include, for example, transformation with Epstein Barr Virus, oncogenes, or retroviruses, or other methods well known in the art. Colonies arising from single immortalized cells are screened for production of antibodies of the desired specificity and affinity for the antigen, and the yield of the monoclonal antibodies produced by such cells may be enhanced by various techniques including, for example, injection into the peritoneal cavity of a vertebrate host.

"Specifically binds" refers to a binding reaction between an antibody and an antigen which is determinative of the presence of the antigen in the presence of a heterogeneous population of proteins and other biologics.

DETAILED DESCRIPTION OF THE INVENTION AND PREFERRED EMBODIMENT

It has now been discovered that an hlyA gene, an hlyB gene and an intergenic region between the hlyA and hlyB genes are present in enterohemorrhagic *E. coli* associated with enterohemorrhagic colitis (EC) and hemolytic uremic syndrome (HUS), but absent in bacteria not associated with such diseases. Moreover, it has been determined that a direct correlation exists between the presence of the hlyA and hlyB genes and the disease symptoms of EC or HUS, regardless of serogroup, slt-I, slt-II or uidA type or, O157:H7 serogroup. As such, it has further been discovered that the hlyA gene, the hlyB gene and the intergenic region between the hlyA and hlyB genes can be used as targets for the specific detection of enterohemorrhagic *E. coli* bacterial pathogens and, in particular, O157:H7 *E. coli*.

As such, in one aspect of the present invention, isolated nucleic acid sequences, corresponding to the hlyA gene, the hlyB gene and the intergenic region between the hlyA and hlyB genes, and novel peptides encoded by these nucleic acid sequences are provided. More particularly, the present invention provides an isolated DNA sequence encoding a peptide having the amino acid sequence of Sequence I.D. No. 2, and an isolated DNA sequence encoding a peptide having the amino acid sequence of Sequence I.D. No. 5. In addition, the present invention provides an isolated DNA sequence, the DNA sequence being the intergenic region between the hlyA gene and the hlyB gene and consisting of the nucleic acid sequence of Sequence I.D. No. 3. Moreover, the present invention provides an isolated, substantially purified DNA sequence specifically hybridizing, under stringent conditions, to a member selected from the group consisting of the hlyA gene, the hlyB gene, the intergenic region between the hlyA gene and the hlyB gene or, combinations or fragments thereof within an *E. coli* genomic or plasmid library, the DNA sequence consisting of a nucleic acid sequence selected from the group consisting of Sequence I.D. No. 1, Sequence I.D. No. 3, Sequence I.D. No. 4, combinations thereof or, fragments thereof.

This aspect of the present invention relies on the use of conventional techniques and procedures in the field of recombinant genetics. Two text books which describe in great detail the general methods of use in this invention are Sambrook, et al., *Molecular Cloning, A Laboratory Manual* (Cold Spring Harbor Publish., Cold Spring Harbor, N.Y. 2nd ed. (1989)), *Methods in Enzymology*, Vol. 152: *Guide to Molecular Cloning Techniques* (Berger and Kimmel (eds.), San Diego: Academic Press, Inc. (1987)) and Kriegler, *Gene Transfer and Expression: A Laboratory Manual* (W. H. Freeman, N.Y. (1990)), both of which are incorporated herein by reference.

The nucleic acid compositions of the present invention, whether RNA, cDNA, genomic DNA or, a hybrid of the various combinations, may be isolated from natural sources or may be synthesized in vitro. The nucleic acids claimed may be present in transformed or transfected whole cells, in a transformed or transfected cell lysate or, in a partially purified or substantially pure form.

Recombinant DNA techniques can be used to produce the peptides encoded by the hlyA and hlyB genes. Briefly, the DNA encoding these peptides are first cloned or isolated in a form suitable for ligation into an expression vector. After ligation, the vectors containing the DNA fragments or inserts are introduced into a suitable host cell for expression of the recombinant peptides. Subsequently, the peptides are isolated from the host cells.

In general, the nucleic acid sequences of the hlyA and hlyB genes encoding the peptides of the present invention are cloned from DNA sequence libraries that are made to encode complementary DNA (i.e., cDNA), genomic DNA or, plasmid DNA. Such libraries may be obtained from commercial sources or, alternatively, they may be prepared from bacteria using techniques known to those skilled in the art. The particular nucleic acid sequences of the hlyA and hlyB genes can be located by hybridizing with an oligonucleotide probe, the sequences of which can be derived from Sequence I.D. Nos.: 1, 3 and 4. The desired target sequences may also be obtained using polymerase chain reaction (PCR) primers which amplify either the entire gene, cDNA or, portions thereof. PCR primers can be selected from the sequences provided herein. Alternatively, where the sequence is cloned into an expression library, the expressed recombinant peptides can be detected immunologically with antisera or, purified antibodies made against the peptide.

To make the cDNA library, one should choose a source that is rich in mRNA. The mRNA can then be made into cDNA, ligated into a recombinant vector, and transfected into a recombinant host for propagation, screening and cloning. Methods for making and screening cDNA libraries are well known. See, Gubler and Hoffman, (*Gene*

25:263–269 (1983)), Sambrook, et al., supra, and Berger and Kimmel, (1987), supra.

For a genomic or plasmid library, the DNA is extracted from the bacteria and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro, as described in Sambrook, et al., supra, and Berger and Kimmel, (1987), supra Recombinant phage are analyzed by plaque hybridization as described in Benton and Davis (*Science*, 196:180–182 (1977)). Colony hybridization is carried out as generally described in Grunstein, et al. (*Proc. Natl. Acad. Sci. U.S.A.* 72:3961–3965 (1975)).

An alternative method combines the use of synthetic oligonucleotide primers with polymerase extension on an mRNA or DNA template. This polymerase chain reaction (PCR) method amplifies nucleic acid sequences of the hlyA and hlyB genes directly from mRNA, from cDNA, from genomic libraries or, cDNA libraries. Restriction endonuclease sites can be incorporated into the primers. The polymerase chain reaction or other in vitro amplification methods may also be useful, for example, to clone nucleic acid sequences of the hlyA and hlyB genes that code for the peptides to be expressed, to make nucleic acids to use as probes for detecting the presence of EHEC mRNA in physiological samples, for nucleic acid sequencing or, for other purposes. U.S. Pat. Nos. 4,683,195 and 4,683,202 describe this method. Genes amplified by the PCR reaction can be purified from agarose gels and cloned into an appropriate vector.

Appropriate primers and probes for amplifying and identifying the peptides encoded by the hlyA and hlyB genes are generated from comparisons of the sequences provided herein. In brief, oligonucleotide primers are complementary to the borders of the DNA region to be amplified are synthesized. The polymerase chain reaction is then carried out using the two primers. For a general overview of PCR, see, e.g., *PCR Protocols: A Guide to Methods and Applications* (Innis, Gelfand, Sninsky and White, eds.), Academic Press, San Diego (1990), incorporated herein by reference.

Oligonucleotides that are useful as probes can be chemically synthesized according to the solid phase phosphoramidite triester method first described by Beaucage and Caruthers (*Tetrahedron Letts.* 22(20):1859–1862 (1981)) using an automated synthesizer, as described in Van Devanter, et al. (*Nucleic Acids Res.* 12:6159–6168 (1984)). Purification of oligonucleotides can be by, for example, native acrylamide gel electrophoresis or, by anion-exchange HPLC as described by Pearson and Reanier (*J. Chrom.* 255:137–149 (1983)).

The sequences of the cloned genes and synthetic oligonucleotides can be verified using the chemical degradation method of Maxam and Gilbert (*Methods in Enzymology* 65:499–560 (1980)). The sequence can be confirmed after the assembly of the oligonucleotide fragments into the double-stranded DNA sequence using the method of Maxam and Gilbert, supra, or the chain termination method for sequencing double-stranded templates of Wallace, et al. (*Gene* 16:21–26 (1981)). Southern Blot hybridization techniques are carried out according to Southern, et al. (*J. Mol. Biol.*, 98:503 (1975)).

Synthetic oligonucleotides can also be used to construct the hlyA and hlyB genes. This is done using a series of overlapping oligonucleotides usually 40–120 bp in length, representing both the sense and nonsense strands of the gene. These DNA fragments are then annealed, ligated and cloned. Moreover, the hlyA and hlyB genes, i.e., polynucleotides, encoding the peptides of the present invention can be cloned using intermediate vectors before transformation into mammalian cells for expression. These intermediate vectors are typically prokaryote vectors or shuttle vectors. The peptides encoded by the hlyA and hlyB genes can be expressed in either prokaryotes or eukaryotes.

In summary, the hlyA and hlyB genes of the present invention can prepared by probing or amplifying select regions of a mixed cDNA, genomic or plasmid pool using the probes and primers generated from the sequences provided herein.

Once the polynucleotides encoding the desired peptides are isolated and cloned, one may express such peptides in a recombinantly engineered cell such as bacteria, yeast, insect (especially employing baculoviral vectors), and mammalian cells. It is expected that those of skill in the an are knowledgeable in the numerous expression systems available for expression of the DNA encoding the peptide of interest. As such, no attempt to describe in detail the various methods known for the expression of proteins in prokaryotes or eukaryotes will be made.

Briefly, however, the expression of natural or synthetic nucleic acids encoding the polypeptides encoded by the hlyA and hlyB genes will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulating the expression of the DNA encoding the peptides of interest. To obtain high level expression of a cloned gene, it is desirable to construct expression plasmids which contain, at the minimum, a strong promoter to direct transcription, a ribosome binding site for translational initiation, and a transcription/translation terminator.

As previously explained, the techniques for nucleic acid manipulation of the hlyA and hlyB genes encoding the peptides of the present invention, such as subcloning nucleic acid sequences encoding peptides into expression vectors, labelling probes, DNA hybridization, and the like are described generally in Sambrook, et al., supra, and Berger and Kimmel, (1987), supra, both of which are incorporated herein by reference.

In another aspect, the present invention provides a method for detecting the presence of enterohemorrhagic *E. coli* in a sample, the method comprising: (a) contacting the sample, under hybridization conditions, with a nucleic acid probe that selectively hybridizes to a member selected from the group consisting of the hlyA gene, the hlyB gene, the intergenic region between the hlyA gene and hlyB gene, or combinations or fragments thereof to form a hybridization complex; and (b) detecting the formation of the hybridization complex as an indication of the presence of enterohemorrhagic *E. coli* in the sample.

Nucleic acid hybridization technology is well known and, thus, no attempt will be made herein to provide a detailed overview of this technology. Many commercial kits are presently available which utilize nucleic acid hybridization to detect microorganisms. A good review of this technology can be found in *Nucleic Acid Hybridization*, A Practical Approach (Hames and Higgins (eds.), IRL Press., pp. 18–30, 1985). See also, U.S. Pat. No. 4,886,741, columns 4–7, which is incorporated herein by reference.

In one aspect of the above method, the nucleic acid probe is one that targets, i.e., selectively hybridizes, to the hlyA gene. Such nucleic acid probes include, but are not limited to, those probes that consists essentially of a nucleic acid sequence which binds, under hybridization conditions which permit specific binding, to a sequence of the hlyA gene selected from the group consisting of the following:

5'-CTGTTTCCCAGAATAAAGCTT-3' (Sequence I.D. No. 6);

5'-AGTCTGTCAACAGCAATTTCA-3' (Sequence I.D. No. 7);

5'-CAGAATATTATAAGCTCCGTGTG-3' (Sequence I.D. No. 8);

5'-GACATCATTTGACTCATTAAA-3' (Sequence I.D. No. 9);

5'-TTTAATGAGTCAAATGATGTC-3' (Sequence I.D. No. 10);

5'-CAAATGATGTCAATGGGATAA-3' (Sequence I.D. No. 11);

5'-TGACAGAATATTATAAGCTCCGTGTG-3' (Sequence I.D. No. 12);

5'-TCATTTAATGAGTCAAATGATGTCAATG-3' (Sequence I.D. No. 13); and

5'-AGTCAAATGATGTCAATGGGATAACATT-3' (Sequence I.D. No. 14).

It will be readily apparent to those of skill in the art that effective probes can be constructed not only from the foregoing subsequences of the hlyA gene, but from sequences which are contained within them, from sequences which overlap them substantially, that is, by approximately 10 base pairs (bp) or more, from other sequences within the hlyA gene, and from sequences that overlap the target gene. The probe may, for example, overlap a portion of the hlyA gene and a portion of the intergenic region between the hlyA gene and the hlyB gene. Presently preferred probes that can be used to target the hlyA gene include, but are not limited to, probes that consist of all or a substantial part of a nucleic acid segment selected from the group consisting of:

5'-AAGCTTTATTCTGGGAAACAG-3' (Sequence I.D. No. 15);

5'-TGAAATTGCTGTTGACAGACT-3' (Sequence I.D. No. 16);

5'-CACACGGAGCTTATAATATTCTG-3' (Sequence I.D. No. 17);

5'-TTTAATGAGTCAAATGATGTC-3' (Sequence I.D. No. 18);

5'-GACATCATTTGACTCATTAAA-3' (Sequence I.D. No. 19);

5'-TTATCCCATTGACATCATTTG-3' (Sequence I.D. No. 20);

5'-CACACGGAGCTTATAATATTCTGTCA-3' (Sequence I.D. No. 21);

5'-CATTGACATCATTTGACTCATTAAATGA-3' (Sequence I.D. No. 22); and

5'-AATGTTATCCCATTGACATCATTTGACT-3' (Sequence I.D. No. 23).

Moreover, suitable probes for targeting the hlyA gene include those which are the chemical and functional equivalent of the foregoing exemplary probes.

In another aspect of the above method, the nucleic acid probe is one that targets, i.e., selectively hybridizes to, the hlyB gene. Presently preferred nucleic acid probes include, but are not limited to, probes that consist essentially of a nucleic acid sequence which binds, under hybridization conditions which permit specific binding, to a sequence of the hlyB gene selected from the group consisting of the following:

5'-GAGAACTACATTTACTCATCAT-3' (Sequence I.D. No. 24); and

5'-CTTCTGGTTACGTCAAGAGCAA-3' (Sequence I.D. No. 25).

It will be readily apparent to those of skill in the art that effective probes can be constructed not only from the foregoing subsequences of the hlyB gene, but from sequences which are contained within them, from sequences which overlap them substantially, that is, by approximately 10 bp or more, from other sequences within the hlyB gene, and from sequences that overlap the target gene. The probe may, for example, overlap a portion of the hlyB gene and a portion of the intergenic region between the hlyA gene and the hlyB gene. Presently preferred probes that can be used to target the hlyB gene include, but are not limited to, probes that consist of all or a substantial part of a nucleic acid segment selected from the group consisting of:

5'-ATGATGAGTAAATGTAGTTCTC-3' (Sequence I.D. No. 26); and

5'-TTGCTCTTGACGTAACCAGAAG-3' (Sequence I.D. No. 27).

Moreover, suitable probes for targeting the hlyB gene include those which are the chemical and functional equivalent of the foregoing exemplary probes.

In a further aspect of the above method, the nucleic acid probe is one that selectively hybridizes to the intergenic region between the hlyA gene and the hlyB gene. Suitable nucleic acid probes include, but are not limited to, those probes that consists essentially of a nucleic acid sequence which binds, under hybridization conditions which permit specific binding, to a sequence of the intergenic region between the hlyA gene and the hlyB gene consisting of all or a substantial part of the following:

5'-ATAACGATGACCATTCCTCCTGGAATG-GCCATCACCTCCTCTTTTAGTC-3' (Sequence I.D. No. 28).

It will be readily apparent to those of skill in the art that effective probes for targeting the intergenic region between the hlyA gene and the hlyB gene can be constructed not only from the from the foregoing sequence, but from sequences which are contained within it, from sequences which overlap it, that is, by approximately 10 bp or more, and from sequences that overlap the intergenic region between the hlyA gene and the hlyB gene. The probe may, for example, overlap a portion of the hlyA gene or, alternatively, the hlyB gene and a portion of the intergenic region between the hlyA gene and the hlyB gene. A presently preferred probe that can be used to target the intergenic region between the hlyA gene and the hlyB gene consists of all or a substantial part of:

5'-GACTAAAAGAGGAGGTGATGGCCATTC-CAGGAGGAATGGTCATCGTTAT-3' (Sequence I.D. No. 29)

Moreover, suitable probes for targeting the intergenic region between the hlyA gene and the hlyB gene include those which are the chemical and functional equivalent of the foregoing exemplary probe.

It is helpful to amplify select subsequences of the hlyA gene, the hlyB gene or, the intergenic region between the hlyA and the hlyB genes prior to detection. A number of nucleic acid amplification systems are available. Amplification systems are well known and have been reviewed in *Bio/Technology* 8:290–293 (April 1990), the teachings of which are hereby incorporated by reference. Such amplification systems include, but are not limited to, the following: PCR, ligase amplification and the Qβ replication system.

The detection of enterohemorrhagic *E. coli* preferably takes advantage of PCR to amplify nucleic acid from these bacteria. As such, in another aspect of the present invention, a method for detecting the presence of enterohemorrhagic *E. coli* in a sample is provided, the method comprising: (a) lysing the target cells present in the sample by combining the sample with a lysis solution, thereby releasing nucleic acid from the target cells; (b) selecting a target, present in the target cells, from the group consisting of the hlyA gene, the hlyB gene, the intergenic region between the hlyA gene and the hlyB gene, or combinations thereof, and selecting a target nucleic acid sequence present in the target; (c) incubating the target nucleic acid sequence, under amplification conditions, with a pair of primers and a nucleic acid polymerase such that each primer is complementary to and hybridizes to one of two separated strands of the target nucleic acid sequence and the polymerase extends the primers to make fully double-stranded replicas of the target nucleic acid sequence; and (d) detecting amplified target nucleic acid as an indication of the presence of enterohemorrhagic *E. coli* in the sample.

The detection of enterohemorrhagic *E. coli* using this method of the present invention requires multiple steps. These steps, which will be explained in greater detail hereinbelow, include an adequate sampling procedure to isolate enterohemorrhagic *E. coli* to a suitable degree for detection, a method for lysing the cells to release nucleic acid, a suitable procedure to amplify the target nucleic acid sequences, and a means to detect the amplified sequences. Moreover, to effectively amplify subsequences of the target nucleic acid, PCR requires amplification primers to initiate polymerase extension. Primers are initially selected for their ability to bind to flanking regions of the target nucleic acid. The primers are further selected for low secondary structure and relatively similar thermal melting ($T_m$) points.

A. Lysis of Enterohemorrhagic *E. coli*

The enterohemorrhagic *E. coli* bacterial cells are lysed in a manner which releases essentially all target DNA or RNA. The target nucleic acid is then recovered from such cells so as to be sufficiently free of potentially interfering substances, such as enzymes, low molecular weight inhibitors or, other components that might interfere with enzymatic amplification of the target DNA sequences.

Prior to lysing, the enterohemorrhagic *E. coli* bacterial cells can optionally be cultured in accordance with standard microbiological techniques, such as those described *Bacteriological Analytical Manual* (7th Edition, AOAC International, Arlington, Va. (1992)), the teachings of which are incorporated herein by reference. Culturing bacteria, with or without selective pressure, will ensure the presence of a sufficient number of bacterial cells from which to extract bacterial DNA. Presently preferred culturing techniques involve the use of liquid enrichment media (e.g., Lauryl Tryptose (LST) Broth), rather than solid agar media. (See, e.g., Chapters 1, 4 and 24 of *Bacteriological Analytical Manual*, supra, the teachings of which are incorporated herein by reference.)

A number of different techniques well known to those of skill in the art can be used to lyse the enterohemorrhagic *E. coli*. Mechanical lysis is particularly useful, and can be achieved by sonication or, by multiple freeze/thaw cycles. Cycles of freezing and thawing are more preferred. Chemical means of cell disruption are also operable and include standard lysing means such as lysozymes, osmotic shock, protease K treatment, and detergents. Chemical methods are less preferred because of possible detrimental effects on the PCR process (e.g., inhibition of the Hot Tub® or the Taq® polymerase). The samples can also be heated to denature proteases and nucleases which might interfere with the components of the PCR reaction mixture. Chemical nuclease and protease inhibitors can also be used in combination with heat.

In the case of RNA detection, DNA is destroyed by deoxyribonuclease, cDNA is reverse-transcribed and then target DNA is amplified using, for example, PCR. Following PCR amplification of targeted nucleic acid sequences, amplified targeted DNA is detected by sufficiently sensitive and specific detection methods. Detection can be achieved, for example, by means of suitable hybridization probes. Moreover, quantification of the amplified target DNA sequences may also be carried out, if desired.

It will be understood by those in the art that it is often advantageous to detect RNA since RNA is indicative of living bacteria. Frequently, it is important to distinguish living, i.e., viable, bacteria from non-living bacteria. For example, for an FDA (Food and Drug Administration) enforcement action to be successful on a food harboring EHEC, it is useful to be able to show the viability of the EHEC isolated. Moreover, clinical diagnosis of EHEC-mediated illness would be much helped by an enumeration of viability of EHECs relative to total EHECs. This would, for example, allow the physician to evaluate the success of antibiotic administration in killing EHECs in invaded tissue. In addition, during the infective phase of EHEC disease, it is likely that there will be more hlyAB RNA than DNA, as the bacteria will likely be expressing the virulent factor.

Moreover, when the sample is a complex mixture such as a fecal sample from a patient suspected of being infected with enterohemorrhagic *E. coli* or a food sample carrying EHEC, it may be necessary to isolate the nucleic acid from the complex mixture. A variety of techniques for extracting nucleic acids from biological samples are known in the art. See, e.g., the extraction methods described by Higuchi in "Simple and Rapid Preparation of Samples for PCR" in *PCR Technology* (Erlich (ed.), Stockton Press (1989)); Maniatis et al., 1989, *Molecular Cloning: A Laboratory Manual*, (New York, Cold Spring Harbor Laboratory, 1982; Hagelberg and Sykes, 1989, *Nature* 342:485; and Arrand, Preparation of Nucleic Acid Probes in *Nucleic Acid Hybridization, A Practical Approach* (Hames and Higgins (eds.), IRL Press., pp. 18–30 (1985)), all of which are incorporated herein by reference. Whole nucleic acid extraction procedures typically involve an initial contacting with phenol, phenol/chloroform or guanidinium salts, followed by an alcohol precipitation. Genomic and plasmid DNA may be obtained from a whole nucleic acid extraction by using RNase before further alcohol precipitation.

B. PCR Procedures

Although PCR is well known in the art (See, U.S. Pat. Nos. 4,683,195 and 4,683,202, the teachings of which are incorporated herein by reference) and although a variety of commercial vendors sell PCR reagents and publish PCR protocols, some general PCR information is provided hereinbelow for purposes of clarity and for a full understanding of the invention to those unfamiliar with PCR.

To begin the PCR process, the target nucleic acid in the sample is denatured (assuming the sample nucleic acid is double-stranded). Denaturation is typically achieved by heating the samples. This is because chemical denaturants may inhibit the polymerase activity.

Once the strands are separated, the next step in PCR involves hybridizing the separated strands with primers that flank the target region or subsequence. The primers are then extended to form complementary copies of the target strands, and the cycle of denaturation, hybridization, and extension is repeated as many times as necessary to obtain the desired amount of amplified nucleic acid.

Template-dependent extension of primers in PCR is catalyzed by a polymerizing agent in the presence of adequate amounts of four deoxyribonucleotide triphosphates (i.e., dATP, dGTP, dCTP, and dTTP) in a reaction medium comprised of the appropriate salts, metal cations and pH buffering system. Suitable polymerizing agents are enzymes known to catalyze template-dependent DNA synthesis. For example, if the template is RNA, a suitable polymerizing agent to convert the RNA into a complementary DNA (cDNA) sequence is reverse transcriptase (RT), such as avian myeloblastosis virus RT or Murine Moloney Leukemia Virus (MMLV) RT. Once the target for amplification is DNA, suitable polymerases include, for example, *E. coli* DNA polymerase I or its Klenow fragment, $T_4$ DNA polymerase, Hot Tub® (Amersham Interantional), and Taq polymerase, a heat stable DNA polymerase isolated from *Thermus aquaticus* and commercially available. The latter enzymes, Hot Tub® and Taq DNA polymerase, are widely used in the amplification and sequencing of nucleic acids. The reaction conditions for using DNA polymerases are known to those in the art and are described in, for example, the treatise *Methods in Enzymology*, supra and in the treatise *Molecular Cloning: A Laboratory Manual*, supra.

During the PCR process, the temperature of the amplification reaction mixture is very carefully controlled so that strand separation and primer annealing and extension occur in equilibrium. The reaction mixture is repeatedly cycled between (1) a low temperature, generally of from about 37° to 70° C., for primer annealing to the selected target sequence for strand reassociation, (2) an intermediate temperature, generally of from about 70° to 80° C., for polymerase extension of the primers, and (3) a higher temperature, generally of from about 80° to 100° C., for denaturation or separation of the strands. Although three temperature ranges have been described, it is often possible that the amplification process can be adequately conducted between two of the temperature ranges. Each thermal cycle of the two or three temperatures can increase the concentration of the amplified target DNA sequence as much as two-fold, so that every series of ten amplification cycles can increase the concentration as much as 1024-fold.

In the preferred embodiment of the PCR process, the reaction is catalyzed by a thermostable DNA polymerase enzyme. The preferred thermostable polymerases are the Hot Tub® polymerase (Amersham International) and the Taq DNA polymerase purified from the bacterium *Thermus aquaticus*. The PCR reaction is carried out at an elevated temperature. The preferred temperature is one at which the enzyme is thermostable, and at which the nucleic acids are in an equilibrium of single and double strands, so that sufficient primer will anneal to template strands to allow a reasonable rate of polymerization. Strand separation is achieved by heating the reaction to a sufficiently high temperature for sufficient time to cause the denaturation of the duplex, but not to cause an irreversible denaturation of the polymerase. If Hot Tub® or Taq is used, the polymerase reaction can be cycled many times, typically 20–40 times, between the two or three temperatures without need to augment the initially added polymerase enzyme.

The PCR method can be performed in a step-wise fashion, where after each step new reagents are added or, in a fashion where all of the reagents are added after a given number of steps. For example, if strand separation is induced by heat, and the polymerase is heat-sensitive, then the polymerase will have to be added after every round of strand separation. However, if, for example, a helicase is used for denaturation or, if a thermostable polymerase is used for extension, then all of the reagents may be added initially. Alternatively, if molar ratios of reagents are of consequence to the reaction, the reagents may be replenished periodically as they are depleted by the synthetic reaction.

Those skilled in the art will know that PCR is generally carried out as an automated process with a thermostable enzyme. In this process, the reaction mixture is cycled through a denaturing step, a primer annealing step, and an extension step. A DNA thermocycler, a machine specifically adapted for use with a thermostable enzyme, is disclosed more completely in EP 236,069 and U.S. Pat. No. 4,889,819. DNA Thermocyclers are commercially available from a number of different sources.

A preferred mode for carrying out the PCR reaction is the multiplex mode. The multiplex mode involves the simultaneous amplification of different target regions using more than one set of PCR primer pairs. The multiplex procedure is preferably designed around primer pairs which have similar thermal melting ($T_m$) points. It is preferred that all pairs have $T_m$s within 8° C. of each other, and that the average $T_m$ is between about 45° C. and about 70° C., with preference for an average $T_m$ of between 60° C. and 70° C.

More particularly, after recovery of substantially undegraded target DNA in a small volume of about 50 µl of water or aqueous buffer, and after selection of the appropriate oligonucleotide primer pair for the targeted DNA sequence, the target DNA is incubated with dNTP's, $Mg^{+2}$, a DNA polymerase and the oligonucleotide primers under conditions where the primers hybridize to the separated (i.e., denatured) target DNA strands and the polymerase extends the primers to make fully double-stranded replicas of the target sequence.

The PCR amplification conditions, such as temperatures, incubation times, solvents, enzyme choice, reagent concentrations, equipment and the like, are chosen to give efficient and specific amplification of the target DNA sequence. It will be readily understood that the effective and optional conditions for each process step and parameter will differ significantly between the targets, the various kinds of test samples, target DNA sequence and primer pairs selected. Solvent choice, enzyme choice and concentration, primer concentration, dNTP concentration, and equipment choice for performing thermal cycles with sufficiently well controlled temperatures and incubation times are generally understood by those skilled in the an of PCR amplification of DNA.

Choice of optimum temperatures and incubation times for the specific target sequences of the invention may be determined by routine titration, monitoring the quantity and quality of amplified DNA, such as by agarose or polyacrylamide gel electrophoresis after staining of DNA with a fluorescent dye such as ethidium bromide. Reaction conditions are selected to maximize the yield of an electrophoretic band of target DNA with the size expected to be defined by the chosen primers and to minimize or, preferably, completely prevent amplification of any other DNA.

C. Selection of Enterohemorrhagic *E. coli* Specific Primers

To effectively amplify subsequences of the target nucleic acid, PCR requires amplification primers to initiate polymerase extension. As previously explained, primers are initially selected for their ability to bind to flanking regions of the target nucleic acid. The primers are further selected for low secondary structure and relatively similar thermal melting ($T_m$) points.

In accordance with the above method of the present invention, suitable primer pairs consist of a "sense" primer selected from the group consisting of:

RH26 5'-AAGCTTTATTCTGGGAAACAG-3' (Sequence I.D. No. 15);
RH28 5'-CACACGGAGCTTATAATATTCTG-3' (Sequence I.D. No. 17);
RH29 5'-TTTAATGAGTCAAATGATGTC-3' (Sequence I.D. No. 18);
RH32 5'-ATGATGAGTAAATGTAGTTCTC-3' (Sequence I.D. No. 26); and
RH35 5'-CACACGGAGCTTATAATATTCTGTCA-3' (Sequence I.D. No. 21); and an "antisense" primer selected from the group consisting of:
RH27 5'-TGAAATTGCTGTTGACAGACT-3' (Sequence I.D. No. 16);
RH30 5'-GACATCATTTGACTCATTAAA-3' (Sequence I.D. No. 19);
RH31 5'-TTATCCCATTGACATCATTTG-3' (Sequence I.D. No. 20);
RH33 5'-TTGCTCTTGACGTAACCAGAAG-3' (Sequence I.D. No. 27);
RH36 5'-CATTGACATCATTTGACTCATTAAATGA-3' (Sequence I.D. No. 22); and
RH37 5'-AATGTTATCCCATTGACATCATTTGACT-3' (Sequence I.D. No. 23).

More particularly, suitable primer pairs include, but are not limited to, the following: RH 26 in combination with RH 27; RH 26 in combination with RH 30; RH 26 in combination with RH 31; RH 26 in combination with RH 33; RH 26 in combination with RH 36; RH 26 in combination with RH 37; RH 27 in combination with RH 28; RH 27 in combination with RH 29; RH 27 in combination with RH 32; RH 28 in combination with RH 30; RH 28 in combination with RH 31; RH 28 in combination with RH 33; RH 28 in combination with RH 36; RH 28 in combination with RH 37; RH 29 in combination with RH 31; RH 29 in combination with RH 33; RH 30 in combination with RH 32; RH 31 in combination with RH 32; RH 32 in combination with RH 33; RH 35 in combination with RH 30; RH 35 in combination with RH 31; RH 35 in combination with RH 33; RH 35 in combination with RH 36; RH 35 in combination with RH 37, etc. It will be readily apparent to those of skill in the art that primer pairs, in addition to those listed, can be generated based on the nucleic acid sequences provided herein. Presently preferred primer pairs include RH 28 in combination with RH 30, and RH 35 in combination with RH 37.

It will be readily apparent to those of skill in the art that effective primers can be constructed not only from the foregoing subsequences, but from sequences which are contained within them, from sequences which overlap them substantially, that is by 10 bp or more, from other sequences present in the target and from sequences that encompass the target. Moreover, it will be readily apparent to those of skill that other suitable primer pairs can be generated, i.e., produce, from a comparison of the nucleic acid sequences provided herein.

D. Detection of Non-Amplified Probe/Target Complex or Amplified Product.

The methods for the detection of a non-amplified target gene subsequence and an amplified target gene subsequence are essentially the same. The only distinction is that the non-amplified target is generally not available in sufficient amounts to permit the use of less sensitive detection means. For example, the detection of the target sequences can, for example, be accomplished by direct visualization of a gel following ethidium bromide staining or, by indirect means using specific nucleic acid hybridization probes. The indirect means are more sensitive and, thus, are recommended for the detection of both amplified and non-amplified targets. Detection methods are well known to those of skill and a general review of such techniques can be found in *Nucleic Acid Hybridization, A Practical Approach* (Hames and Higgins (eds.), IRL Press, Washington, D.C. (1985)). As such, no attempt to describe in detail each and every possible detection method will be made.

When detection of the target gene subsequence is by hybridization as in a Southern blot for example, nucleic acid probes specifically complementary to a subsequence of the amplified region are used. Such probes are readily obtainable from the sequence of the amplified segment. Probes preferably hybridize to a DNA subsequence located between the primer binding subsequences to avoid any overlap of the probe sequence with the primer sequences. The preferred probes for use with the primers of the present invention include, for example, those set forth above with respect to the method for detecting enterohemorrhagic *E. coli* using nucleic acid hybridization techniques. However, those of skill will readily recognize that other nucleic acid probes varying in length and in binding sites can also be used for detection purposes.

Probes may be labeled by any one of several methods typically used to detect the presence of the amplified product, i.e., the amplicon or hybridization duplex. The most common method of detection is the use of autoradiography with $^3$H, $^{125}$I, $^{35}$S, $^{14}$C, or $^{32}$P labeled probes or, the like. The choice of radioactive isotope depends on preferences due to ease of synthesis, stability and half lives of the selected isotopes. Other labels include ligands which bind to antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The choice of label dictates the manner in which the label is bound to the probe. The probes can be labeled using radioactive nucleotides in which the isotope resides as a part of the nucleotide molecule, or in which the radioactive component is attached to the nucleotide via a terminal hydroxyl group that has been esterified to a radioactive component such as inorganic acids, e.g., $^{32}$P phosphate or $^{14}$C organic acids or, esterified to provide a linking group to the label. Base analogs having nucleophilic linking groups, such as primary amino groups, can also be linked to a label.

Non-radioactive probes are often labeled by indirect means. For example, a ligand molecule is covalently bound to the probe. The ligand then binds to an anti-ligand molecule which is either inherently detectable or, covalently bound to a detectable signal system, such as an enzyme, a fluorophore or, a chemiluminescent compound. Ligands and anti-ligands may be varied widely. Where a ligand has a natural anti-ligand, namely ligands such as biotin, thyroxine, and cortisol, it can be used in conjunction with its labeled, naturally occurring anti-ligands. Alternatively, any haptenic or antigenic compound can be used in combination with an antibody.

Probes can also be labeled by direct conjugation with a label. For example, cloned DNA probes have been coupled directly to horseradish peroxidase or alkaline phosphatase, (Renz. M., and Kurz, K., "A Colorimetric Method for DNA Hybridization," *Nuc. Acids Res.* 12:3435–3444 (1984)), and synthetic oligonucleotides have been coupled directly with alkaline phosphatase (Jablonski, et al., "Preparation of Oligodeoxynucleotide-Alkaline Phosphatase Conjugates and Their Use as Hybridization Probes," *Nuc. Acids. Res.* 14:6115–6128 (1986)).

Enzymes of interest as labels will primarily be hydrolases, such as phosphatases, esterases and glycosidases or, oxidoreductases, particularly peroxidases. Fluorescent compounds include fluorescein and its derivatives, rhodamine and its derivatives, dansyl, umbelliferone, etc. Chemiluminescers include luciferin, and 2,3-dihydrophthalazinediones, e.g., luminol.

A preferred mode of detecting amplified DNA target sequences is via hybridization to a single-stranded oligonucleotide probe which is sequence-complementary to a DNA subsequence located between the two selected oligonucleotide primers in the target sequence. If the amplified DNA target sequence is denatured and captured on a solid support, such as nylon or nitrocellulose membrane, the probe may be radioactively tagged or attached directly or indirectly to an enzyme molecule. Then, after incubation of membrane-captured amplified target DNA sequence product with the probe under hybridization conditions, excess probe can be washed away and detection can be by autoradiography or radiation counting, radioactive probe or, by exposure to a chromogenic or fluorogenic substrate of the probe-attached enzyme. If the oligonucleotide hybridization probe has been attached to a solid support, the incubation of denatured amplified target DNA sequence product with the solid support under hybridization conditions results in immobilization of the amplified product. If the product contains biotin or, some other chemical group for which there are specific binding molecules, like avidin and antibodies, then the immobilized amplified product can be detected with an enzyme attached to the specific binding molecule, such as horseradish peroxidase or alkaline phosphatase attached to streptavidin.

Amplified target DNA can also be detected by high pressure liquid chromatography, i.e., HPLC. Separation of the amplified PCR target DNA product, side products, and unreacted reagents by HPLC can provide a rapid quantitative report on the presence or absence of amplified DNA of the expected size range. HPLC columns may, for example, be based on ion exchange, paired-ion reverse-phase or, size exclusion separations. The column effluent is generally most simply detected and quantified by ultraviolet absorbance in the 250–280 nm spectral region, although fluorescent monitoring, after post-column derivatization with a fluorescent DNA-binding dye, and electrochemical detection also are possible and generally are potentially more sensitive than spectrophotometry. Separation of amplified PCR target DNA product, side products, and unreacted reagents by gel electrophoresis, followed by DNA staining with a fluorescent or absorbing dye, also reports on the presence or absence of amplified DNA in the expected size range. The electrophoresing conditions and the means for detecting the individual amplified oligonucleotides are well known and are not critical aspects of this invention. Alternatively, the amplicon, i.e., the PCR amplification product, could be sequenced using conventional methods and techniques. There could be variants of hlyAB among EHECs and sequencing the amplicons' DNA would provide useful information which could be used, for example, for epidemiological studies or, for deriving additional primers that could be used to detect specific hlyAB strains. Any of the means accepted by those of skill can be used for detection in this invention.

In a further aspect of the present invention, kits suitable for use in carrying out the PCR amplification and detection methods of the present invention are provided. Such test kits, designed to facilitate the amplification and detection of enterohemorrhagic *E. coli*, will generally comprise a primer pair consisting of two oligonucleotide primers complementary to about 10–30 nucleotide sequences on complementary strands of a targeted RNA or DNA sequence in a target gene of the EHEC, and a probe sequence for detection of a targeted subsequence and, optionally, a control template of the targeted subsequence.

The test kits may further comprise published instructions and reagents for the PCR amplification and detection of the targeted sequence. Reagents for the PCR amplification of the targeted RNA or DNA subsequence would include: deoxyribonuclease, reverse transcriptase, PCR amplification polymerase and the like. In addition, the kits may also include a bulk polymerase chain amplification reaction mix which would contain optimized concentrations of the DNA Polymerase, a thermal resistant nucleic acid polymerase, select primers, dNTPs, and buffer salts.

In a final aspect of the present invention, a method is provided for detecting the presence of enterohemorrhagic *E. coli* in a sample, the method comprising: (a) contacting the sample with a substantially purified immunoglobulin that specifically binds a peptide encoded by a gene selected from the group consisting of the hlyA gene and the hlyB gene; and (b) detecting the bound immunoglobulin. In presently preferred embodiments, the peptide has the amino acid sequence of Sequence I.D. No. 2 or, alternatively, of Sequence I.D. No. 5.

As such, in addition to the detection of the hlyA gene, the hlyB gene or the intergenic region between the hlyA and hlyB genes using nucleic acid hybridization technology, one can use immunoassays to detect either the products of the hlyA and hlyB genes or, the presence of antibodies to such products. Immunoassays can be used to qualitatively or quantitatively analyze the products of the products of the hlyA and hlyB genes or antibodies to such products. A general overview of the applicable technology can be found in Harlow and Lane, *Antibodies: A Laboratory Manual* (Cold Spring Harbor Pubs., New York. (1988)), incorporated herein by reference.

a. Antibody Production

A number of immunogens may be used to produce antibodies specifically reactive with peptide antigen. Recombinant peptides encoded by the hlyA or hlyB genes are the preferred immunogens for the production of monoclonal or polyclonal antibodies. Naturally occurring peptides may also be used either in pure or impure form. Synthetic peptides made using the peptide sequences described herein (i.e., Sequence I.D. Nos. 2, and 5) may also be used as an immunogen for the production of antibodies to the peptides encoded by the hlyA and hlyB genes.

Preferentially, a recombinant peptide encoded by either the hlyA and hlyB genes or, a fragment thereof, is expressed in bacterial cells as described above, and purified using conventional techniques known to and used by those of skill in the art. The product is then injected into an animal capable of producing antibodies. Either monoclonal or polyclonal antibodies may be generated, for subsequent use in immunoassays to measure the peptides encoded by hlyA and hlyB.

Methods of production of polyclonal antibodies are known to those of skill in the art. In brief, an immunogen, preferably a purified protein, is mixed with an adjuvant and animals are immunized. The animal's immune response to the immunogen preparation is monitored by taking test bleeds and determining the titer of reactivity to the perilipin protein. When appropriately high titers of antibody to the immunogen are obtained, blood is collected from the animal and antisera is prepared. Further fractionation of the antisera to enrich for antibodies reactive to the peptides encoded by hlyA and hlyB can be done if desired. (See, Harlow and Lane, supra.)

Monoclonal antibodies can be obtained by various techniques familiar to those skilled in the art. Briefly, spleen cells from an animal immunized with a desired antigen are immortalized, commonly by fusion with a myeloma cell (See, e.g., Kohler and Milstein, *Eur. J. Immunol.* 6:511–519 (1976), incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host.

Either monoclonal or polyclonal antibodies specific for the gene product can be used in various immunoassays. Such assays include, for example, ELISA, competitive immunoassays, radioimmunoassays, Western blots, indirect immunofluorescent assays and the like. The reporter molecule used to detect the bound immunoglobulin will depend on the assay used and will be readily apparent to those of skill in the art.

The invention will be described in greater detail by way of specific examples. The following examples are offered for illustrative purposes, and are intended neither to limit or define the invention in any manner.

EXAMPLES

A. General Considerations

N.B. Great care should be taken with bacterial samples and cultures potentially carrying enterohemorrhagic *Escherichia coli*. These organisms have a very low infectious dose, and can be transmitted from person to person. Individuals should not culture these organisms without proper microbiological and safety training.

N.B. Contamination with extraneous bacteria or DNA fragments: The best laboratory practice is necessary to conduct PCR experiments because of the massive amplifications which take place. To this end, preparations with little DNA (reaction mixtures, enzyme, buffer, dNTPs etc) should be stored physically distant from samples rich in DNA (gel boxes, PCR machine, primer preparations, DNA templates etc.) Controls should always be chosen which will detect the occurrence of contamination with extraneous DNA.

N.B. The manufacturer's instructions were used for the following equipment: PCR reactions (Amersham), Gene-Amp 9600 PCR machine (Perkin-Elmer), gel boxes (BRL or Mupid), the transilluminator and Polaroid camera. The methods used herein are standard and within the competency of those of skill in the art.

N.B. It is assumed that those of skill in the art will exercise the proper techniques when using the methods described herein exercise the proper techniques. These include aseptic handling of micro-organisms, and the sterile and axenic handling of DNA, oligonucleotide, and all the other reagents and equipment normally utilized in molecular biology experiments.

B. Materials

1. Luria Broth consists of:

5 g Yeast Extract ((Difco Laboratories, Detroit, Mich.);

10 g Tryptone (0127-01-7 Difco Laboratories, Detroit, Mich.);

5 g NaCl (SX0420-1, EM Science, Gibbstown, N.J.); and distilled Water to 1000 ml.

2. Tris Buffered Saline (TBS) consists of:

0.9% w/v NaCl; and 50 mM Tris HCl pH 7.4.

3. Phosphate Buffered Saline (PBS) (Cat. #3400-1013 Digene Diagnostics Inc., Beltsville, Md.)

4. Lysis Solution consists of:

100 mg of proteinase K (Cat. #P-2308 Sigma Chemical Company, St Louis, Mo.);

200 µl of 30% (w/v) Brij35 (Cat. #430AG-6 Sigma Chemical Company, St Louis, Mo.);

400 µl of 0.5M EDTA (pH 8.0) (Cat. #S-04X-AG Digene Diagnostics Inc., Beltsville, Md.);

400 µl 1M Tris HCl (pH 8.0) (Cat. #S15X-BG Digene Diagnostics Inc., Beltsville, Md.); and 900 µl sterile distilled water. Aliquot into 4 tubes, store at −20° C.

5. Stop Mix:

5 x Gel Loading Buffer: (Cat. #3400-1046 Digene Diagnostics Inc., Beltsville, Md.).

6. Gels consist of:

1% weight/volume (w/v) Agarose (Sigma chemical company, Agarose, Molecular Biology Reagent, Cat #A-9539) dissolved in TBE (Gel-Mix Running Mate Cat. #5546UA, Gibco BRL Life Technologies, Gaithersburg, Md.) and ethidium bromide (Sigma Chemical Company (Cat. #E-7637)) to a final concentration of 10 µg/ml.

C. Preparation of DNA Template

Into sterile Eppendorf tubes is aseptically pipetted 1 ml of sterile Luria Broth. The Eppendorf tubes are capped and labeled.

Bacteria are inoculated into these 1 ml volumes of Luria Broth or, other media suitable for the growth and enrichment of O157:H7 and EHECs using a sterile tooth-pick. (See, *Bacteriological Analytical Manual*, supra.) Until experienced in this method, it is useful to include a growth control *E. coli* strain, such as a K12 serogroup laboratory strain, with which to compare the extent of growth among the test cultures. Bacterial cultures were obtained from agar plates, but inocula could similarly be obtained from an enrichment culture (as described in the *Bacteriological Analytical Manual*, supra) or, inocula could consist of a sample of a food or beverage, for example, milk suspected of harboring EHEC bacteria.

Cultures are incubated at 35°–37° C. overnight (i.e., for about 16–20 hours) either stationary or, with shaking. The tubes are kept with the caps in the closed position.

After overnight incubation, the cultures are observed for turbidity and anomalous growth is noted, such as no growth. Cultures which do not grow should be repeated with due regard to: 1) over-selective pressure in enrichment culture; 2) loss of viability of bacteria in inoculum; 3) loss of control of incubator temperature; 4) special physical or chemical requirements of bacteria in sample; and 5) other factors, such as absence of viable bacteria in sample (e.g., in a sample of well-cooked foods).

The cultures are centrifuged in a Tomy MXT-150 refrigerated microcentrifuge for 5 minutes at 15,000 rpm at 4° C., and the culture supernatant is carefully removed using a pipette, and is disposed of with due regard for the potential pathogenicity of the bacteria remaining in the supernatant.

The bacterial pellet is then observed and the size of the pellet is compared visually to that of the control *E. coli* K12 strain "growth control." Experienced experimenters will be able to ascertain the extent of growth without this step.

The bacterial pellets are then resuspended in between 100 µl and 500 µl of Tris-buffered saline (TBS) or, phosphate buffered saline (PBS). The volume used depends on the extent of bacterial growth. For fully grown cultures, use 500 µl of TBS or PBS. For marginally grown cultures with a bacterial pellet estimated at approximately 20% the size of the *E. coli* K12 control, use 100 µl of PBS or TBS. For intermediate growth, use an intermediate volume. If the pellet appears small or absent, consider carefully the reasons for that before interpreting a negative PCR result.

When fully resuspended, add to each resuspended pellet between about 1 µl to about 5 µl of Lysis Solution, mix quickly but thoroughly, and incubate at either 37° C. or 60° C. for 30 minutes or until the suspension has cleared, i.e., when it does not scatter light to the eye. When clear or after 30 minutes (whichever comes sooner), samples are placed in a water bath at 100° C. for 5 min. After boiling, the samples are observed for clarity (i.e., light scattering) and anomalous observations are noted.

Tubes are surface-dried with a paper wipe, and are stored on ice if they are to be used within 2 hours or, stored at –70° C. to –135° C. for long term storage. This is the DNA template, and it can be aliquotted and frozen for multiple use. Eventually endogenous nucleases will degrade the template DNA to the point where it ceases to produce results consistent with fresh template. However, if stored properly, many uses can be expected.

D. How to Estimate The Correct Temperature For Annealing Reactions

F. Estimation of the Annealing Temperature of the Primers

For each A or T base, count 2° C. For each G or C base, count 4° C. The DNA sequence around the RH 28, RH 30, and RH 31 primers was studied for the appropriate changes.

| Primer | Theor T. | Req. T. | Add °C. | modification: 5' | 3' |
|---|---|---|---|---|---|
| RH28 | 64 | 72 | add 8° C. | — | TCA |
| RH30 | 54 | 72 | add 18° C. | CATT | TGA |
| RH31 | 54 | 72 | add 18° C. | AATG | ACT |

For the two-step cycling, 2-step default parameters for the GeneAmp 9600 PCR machine are used, which include annealing and extension at 68° C., not 72° C. Why use 68° C. and not 72° C.? The reason is that if Perkin-Elmer default the machine to 68° C., that indicates that 68° C. is a better temperature for the enzyme than 72° C., and the data suggest that the higher stringency conferred by increasing the temperature from 68° C. to 72° C. is not necessary.

RH 28 becomes RH 35 with 26 base pairs
RH 30 becomes RH 36 with 28 base pairs
RH 31 becomes RH 37 with 28 base pairs
RH 35: 5'-CAC ACG GAG CTT ATA ATA TTC TGT CA-3'
RH 36: 5'-CAT TGA CAT CAT TTG ACT CAT TAA ATG A -3'
RH 37: 5'-AAT GTT ATC CCA TTG ACA TCA TFT GAC T -3'

| PRIMERS USED: | sense/antisense | Calc. Temp |
|---|---|---|
| RH 26 AAG CTT TAT TCT GGG AAA CAG | sense | 58° C. |
| RH 27 TGA AAT TGC TGT TGA CAG ACT | antisense | 58° C. |
| RH 28 CAC ACG GAG CTR ATA ATA TRC TG | sense | 64° C. |
| RH 29 TIT AAT GAG TCA AAT GAT GTC | sense | 54° C. |
| RH 30 GAC ATC ATT TGA CTC ATT AAA | antisense | 56° C. |
| RH 31 TTA TCC CAT TGA CAT CAT TRG | antisense | 56° C. |
| RH 32 ATG ATG AGT AAA TGT AGT TCT C | sense | 58° C. |
| RH 33 TRG CTC TRG ACG TAA CCA GAA G | antisense | 64° C. |

| PRIMER PAIRS USED: Primer Pair: | Theoretical Temp: | Approx. Fragment Size: |
|---|---|---|
| RH 26/RH 27 | 58/58 – 2 = 56 | 2368 |
| RH 26/RH 30 | 58/56 – 2 = 54 | 2005 |
| RH 26/RH 31 | 58/56 – 2 = 54 | 2000 |
| RH 26/RH 33 | 58/64 – 2 = 56 | 2826 |
| RH 27/RH 28 | 58/64 – 2 = 56 | 700 |
| RH 27/RH 29 | 58/54 – 2 = 52 | 395 |
| RH 27/RH 32 | 58/58 – 2 = 56 | 120 |
| RH 28/RH 30 | 64/56 – 2 = 54 | 340 |
| RH 28/RH 31 | 64/56 – 2 = 54 | 360 |
| RH 28/RH 33 | 64/64 – 2 = 62 | 1200 |
| RH 29/RH 31 | 54/56 – 2 = 52 | 40 |
| RH 29/RH 33 | 54/64 – 2 = 52 | 900 |
| RH 30/RH 32 | 56/58 – 2 = 54 | 480 |
| RH 31/RH 32 | 56/58 – 2 = 54 | 460 |
| RH 32/RH 33 | 58/64 – 2 = 56 | 425 |

E. Making Primers Suitable for Two-Step PCR:

The aim was to increase the annealing temperature of RH 28 and RH 30 in order to use a 2-step PCR process. If the annealing temperature is at the optimum temperature of the enzyme, then both the annealing and extension steps can be accomplished at the same time and at the same temperature, thereby removing one step of the PCR. In selecting suitable primers, aim to have primers with theoretical annealing temperature of 72° C.

G. Diluting Primers: Calculating Concentration and Making to 10 pmol/µl:

Receive lyophilized primers:

Need to dilute to 10 picomoles/µl

Use standard calculation:

X=5×# of Base Pairs divided by total OD units: then multiply by 10 for a 500 µl stock of diluted primer:

X=μl primer
Y=μl water
Example:

|  | A260 | X | 10X | Y |
| --- | --- | --- | --- | --- |
| RH35 | .448 | 5.8 | 58 | 442.0 |
| RH36 | .430 | 6.51 | 65.1 | 434.9 |
| RH37 | .448 | 6.25 | 62.5 | 455.2 |

H. How to Make a PCR Reaction Mixture

It should be noted that the standard protocols for PCR will work quite adequately, and reagents or kits from a range of suppliers can probably be used with effectiveness equal to that described herein.

In all reactions, the PCR kit sold by Amersham International was used according to the manufacturer's instructions. The enzyme used was Amersham's Hot Tub polymerase, the buffer used was that supplied by Amersham with the Hot Tub enzyme, and the dNTPs used were purchased from US Biochemical Corp., Cleveland, Ohio (Cat. #US77100). Typically, reactions were prepared by adding together enough reagents for the number of experiments to be done, with a few spare reactions, to accommodate the vagaries of multiple pipetting.

Thus, for one PCR reaction, the following reagents and volumes are added to a tube entitled "reaction mixture", where ☞ stands for the forward or, sense primer, and ☜ stands for the reverse or, antisense primer:

| Water | 25 μl |
| --- | --- |
| PCR buffer | 5 μl |
| dNTP | 8 μl |
| ☞ | 5 μl |
| ☜ | μl |
| Vol/reaction tube: | 48 μl |

Typically, many PCR reactions are run at the same time. So, for example if 18 reactions are to be run using the same primers, the reaction mixture is made up as described above, but each component is multiplied by 20, rather than 18, to allow for the minor pipetting variations which occur as liquids expand as they warm up from pipetting, and other minor fluctuations in delivery.

|  | 1 reaction | 20 reactions |
| --- | --- | --- |
| Water | 25 μl | 500 μl |
| PCR buffer | 5 μl | 100 μl |
| dNTP | 8 μl | 160 μl |
| ☞ | 5 μl | 100 μl |
| ☜ | 5 μl | 100 μl |
| Vol/reaction tube: | 48 μl | 960 μ |

To each thin-walled Perkin-Elmer reaction tube (specified for use in the GeneAmp 9600 PCR machine), pipette 48 μl of reaction mixture.

On occasions, the experiment calls for several different primer pairs to be tested. In this instance, the "reaction mixture" is made up as described above, but without the PCR primers. The primers are added (5 μl each of the ☞[forward primer] and ☜[reverse primer] to the thin-walled PCR reaction tubes after the reaction mixture (consisting of water, buffer, and dNTPs) has been added.

—To each thin-walled PCR reaction tubes is added 1 μl of Template (prepared as described above).

—The rack containing all the thin-walled PCR reaction tubes is then inserted into heating chamber.

—The GeneAmp 9600 PCR machine is turned on.

—The program or method is selected and run.

I. Methods

Several methods were used in the GeneAmp PCR 9600 PCR machine. The method selected was dependent on the primers and templates being used. In the results set forth herein, the method is listed along with the primer pair used.

The following were frequently used primer/method combinations:

RH28 & RH 30 using Method 12
RH28 & RH 30 using Method 14
RH35 & RH 37 using Method 13

J. PROGRAMS

Hot Start Program:
5=Hot Start: Hold at 94° C. for 7:00 min.
PCR Programs:
6=3 step PCR: 94° C. for 90 sec., 52° C. for 90 sec, 72° C. for 90 sec, no ramping temperatures.
7=2-step PCR: 68° C. anneal & extend, then 94° C. denature; each temperature held for 30 sec, no ramping temperatures, 30 cycles
8=3 step PCR: 94° C. for 90 sec., 54° C. for 90 sec, 72° C. for 90 sec, no ramping temperatures.
Finishing Program:
4=Extension and Finish off ends: 72° C. hold for 7:00 min.
Hold/Soak Program:
1=Hold cold: at 4° C. indefinitely

K. PCR METHODS:

Method 12: programs [5,6,4,1]
Method 13: programs [5,7,4,1] (Completes the PCR reactions in under one hour)
Method 14: programs [5,8,4,1]

Hot Start Program 5:

A "hot start," i.e., the addition of the Hot Tub enzyme to all PCR reactions at the denaturing temperature of 94° C., was carried out. This is accomplished by starting the Methods with program 5, which is a 94° C. hold program for 7 min, during which 0.5 μl of Hot Tub enzyme is added to each reaction tube. After all enzyme additions have been made, the reaction tube caps are tightly affixed, and the heat-block lid is screwed down as described in the instructions. This must be accomplished in the allotted 7 min.

When the PCR Method has reached the Hold/Soak program 1, and the temperature of the block has dropped to approx 4° C., the machine can be turned off or, alternatively, the samples can be left in the machine overnight. When the sample rack is removed any condensation on the machine and rack is dried off. Into each of the PCR reaction tubes is mixed 5 μl of Gel Loading Buffer.

L. Preparation of BRL Gel for Visualization of PCR Amplicons

Samples (25 μl per lane) are run on agarose gels in TBE buffer and ethidium bromide to visualize amplicons. The molecular weight markers used were the 123 base pair ladder of Gibco BRL Life Technologies (Gaithersburg, Md.) (Cat. # 5613SB).

M. Running Samples In BRL Gel Box:

Method: Gels consisting of 1% agarose in TBE with ethidium bromide were prepared as follows: 2.5 g agarose was added to 250 mls of TBE, was mixed, and brought to a boil using the microwave oven, and cooled to 50° C. in a waterbath. Ethidium bromide was added (2.5 μl of stock solution of 10 mg/ml, and the liquid gel was stirred by swirling. When at 50° C. the gel is poured into a gel casting stand (Horizon 20.25 Gel Casting System, BRL, Bethesda, Md.) with two 20-well combs in place, as described in the manufacturer's instructions. Gels are run at 100 Volts for 1 hour, or 140 Volts for 45 min.

N. Running Samples in MUPID Gel Box

Alternative (quicker) method: the MUPID gel apparatus. This apparatus has the advantage of running gels much faster, for example in 10 minutes. Essentially the same protocol is used with the same reagents, except that the gel volumes are much less, typically 50 mls each.

The practicality of this system was demonstrated, although most samples were run in the BRL Horizon gel system because of the more numerous teeth on the combs used in the BRL apparatus. Generally, 100 mls of gel was made up, of 1% w/v agarose in TBE, with 1 µl EtBr stock (of 10 mg/ml). The mixture was brought to a boil and swirled into solution, cooled to 50° C., and gels were cast in the casting stand provided by the manufacturer. Loaded 15 µl of samples to each well, 7.5 µl of 123 base pair ladder to molecular weight ladder tracks. Mupid gels take approximately 10–25 minutes to run.

O. Photographing Gels

Gels were photographed on Polaroid Type 55 positive/negative film, exposure 25 seconds at f 5.6.

EXAMPLE I

EHEC strains from outbreaks in the Pacific North-West. Strains were evaluated using the PCR amplification methods of the present invention. PCR was carried out in accordance with the above protocols.

TABLE I

| Strain | FDA # | Serogroup | State & County | Clin. Symp. | RH35/ 37 PCR | PCR detects EHEC? |
|---|---|---|---|---|---|---|
| 84-01 | 400 | O157:H7 | WA-? | HUS | + | yes |
| 85-08 | 404 | O157:H7 | WA-? | HUS | + | yes |
| 86-17 | 403 | O157:H7 | WA-Kitsap | HUS | + | yes |
| 86-01 | 414 | O157:H7 | WA-? | HUS | + | yes |
| 86-24 | 415 | O157:H7 | WA-Walla Walla | HUS | + | yes |
| 86-28 | 416 | O157:H7 | WA-? | HC | + | yes |
| 87-13 | 406 | O157:H7 | WA-? | HC | + | yes |
| 87-21 | 407 | O157:H7 | WA-? | HUS | + | Yes |
| 87-11 | 405 | O157:H7 | WA-? | HC | + | yes |
| PT 85-05 | 401 | O157:H7 | WA-King | HUS | + | yes |
| PT 86-22 | 413 | O157:H7 | WA-? | HUS | + | yes |
| PT 86-18 | 411 | O157:H7 | WA-? | HC | + | yes |
| PT 85-07 | 408 | O157:H7 | WA-? | HC | + | |
| TB 334 | 402 | O157:H7 | WA-? | D | + | yes |
| TB 285 | 409 | O-:H11 | WA-Snohomish | D | + | yes |
| TB 226 | 410 | O26:H- | WA-King | HC | + | yes |
| TB 352 | 412 | O68:H- | WA-King | D | − | strain dead |
| TB 154 | 399 | O153:H2 | WA-King | D,MA | + | yes |

D = Diarrhea, HUS = hemolytic uremic syndrome, MA = mesenteric adenitis, HC = hemorrhagic colitis

EXAMPLE II

This example involves the amplification and detection of ATCC O157:H7 strains of various SLT types using the protocols set forth above. The various O157:H7 strains of enterohemorrhagic *E. coli* were detected using the methods of the present invention regardless of SLT type.

TABLE II

| ATTC # | Serogroup | SLT type | State | Clinical sym | PCR RESULT |
|---|---|---|---|---|---|
| ATCC3515 /EDL 931 | O157:H7 | NK | NK | HC | + |
| ATCC43888 /CDC B6914-MS1 | O157:H7 | I–II– | NK | NK | + |
| ATCC43889 /CDC B1409-C1 [1271-84] | O157:H7 | I–II+ | NC | HUS | + |
| ATCC43890 /CDC C984 | O157:H7 | I+II– | CA | NK | + |
| ATCC43894 /CDC EDL 932 | O157:H7 | I+II+ | MI | HC | + |
| ATCC43895 /CDC EDL 933 | O157:H7 | I+II+ | NK | HC | + |

NK: not known.

EXAMPLE III

This example involves the amplification and detection of various laboratory control strains using the methods and protocols set forth above.

TABLE III

| Control | Strain # | Expected | Observed | OK? |
|---|---|---|---|---|
| E. coli | HB 101 | − | − | OK |
| clone | XL5 | + | + | OK |
| ETEC | H10407 | − | − | OK |

TABLE III-continued

| Control | Strain # | Expected | Observed | OK? |
|---|---|---|---|---|
| | 1639-78 | + | + | OK |

EXAMPLE IV

A range of bacteria isolated from a wide range of sources were assayed using three PCR methods based on the amplification of EHEC hlyAB sequences. Only EHEC strains associated with typical enterohemorrhagic disease were positive. See, Table IV, supra.

TABLE IV

| Organism | character | RH28/RH30 Meth12 | RH28/RH30 Meth14 | RH35/RH37 Meth13 |
|---|---|---|---|---|
| E. coli WAM 111 | UTI | – | – | – |
| E. coli WAM107 | UTI | – | – | – |
| E. coli J 96 | – | – | – | – |
| E. coli J198 022 | avirulent | – | – | – |
| E. coli 105 | ETEC | – | – | – |
| Klebsiella pneumonias K7 | diarrhea | – | – | – |
| K. pneumonlae K5 | diarrhea | – | – | – |
| Salmonella enteriditis D6800 | salmonellosis | – | – | – |
| S. enteriditis 48-86 | salmonellosis | – | – | – |
| S. enteriditis 464 | salmonellosis | – | – | – |
| S. enteriditis GJ | salmonellosis | – | – | – |
| S. enteriditis C4902 | salmonellosis | – | – | – |
| S. typhimurium GJ | salmonellosis | – | – | – |
| S. dublin 17-86 | salmonellosis | – | – | – |
| S. dublin 254-84 | salmonellosis | – | – | – |
| V. parahaemolyticus 4037 | gastroenteritis | – | – | – |
| V. vulnificus A9 | septicemia | – | – | – |
| Vibrio hollisae SR 501 | gastroenteritis/septicemia | – | – | – |
| V. cholerae 1074 | none | – | – | – |
| V. cholerae 1837 | 0139 cholera | – | – | – |
| V. cholerae E7946 | 01 El Tor cholera | – | – | – |
| V. cholerae 569B | 01 classical cholera | – | – | – |
| Pseudomonas aeruginosa F72 | wound infections | – | – | – |

TABLE IV-continued

| Organism | character | RH28/RH30 Meth12 | RH28/RH30 Meth14 | RH35/RH37 Meth13 |
|---|---|---|---|---|
| E. coli DH5a/K12 | none | | | |
| XL5 clone/K12 w/hlyAB | not known | + | + | + |
| E. coli 401 O157:H7 EHEC | HUS | + | + | + |
| E. coli 402 O157:H7 EHEC | D | + | + | + |
| E. coli 403 O157:H7 EHEC | HUS | + | + | + |
| E. coli 405 O157:H7 EHEC | HC | + | + | + |
| E. coli 374 O157:H7 EHEC (ATCC) | HC | + | + | + |
| E. coli 375 O157:H7 EHEC (ATCC) | not known | + | + | + |
| E. coli 376 O157:H7 EHEC (ATCC) | HUS | + | + | + |
| E. coli 377 O157:H7 EHEC (ATCC) | not known | + | + | + |
| E. coli 378 O157:H7 EHEC (ATCC) | HC | + | + | + |
| E. coli 379 O157:H7 EHEC (ATCC) | HC | + | + | + |
| E. coli 410 O26:H- EHEC | HC | + | + | + |
| E. coli 411 O157:H7 EHEC | HC | + | + | + |

The foregoing is offered for purposes of illustration. It will be readily apparent to those skilled in the art that the operating conditions, materials, procedural steps and other parameters of the methods described herein may be further modified or substituted in ways without departing from the spirit and scope of the invention.

---

What is claimed is:

1. An isolated DNA sequence encoding a peptide having the amino acid sequence of Sequence I.D. No. 2.

2. An isolated DNA sequence in accordance with claim 1 wherein said DNA sequence is operably linked to a nucleic acid sequence thereby forming an operon.

3. An isolated DNA sequence encoding a peptide having the amino acid sequence of Sequence I.D. No. 5.

4. An isolated DNA sequence in accordance with claim 3 wherein said DNA sequence is operably linked to a nucleic acid sequence thereby forming an operon.

5. An isolated, substantially purified DNA sequence specifically hybridizing, under stringent conditions, to a member selected from the group consisting of the hlyA gene, the hlyB gene, the intergenic region between the hlyA gene and the hlyB gene, or combinations thereof within an *E. coli* genomic or plasmid library, said DNA sequence consisting of a nucleic acid sequence selected from the group consisting of Sequence I.D. No. 1, Sequence I.D. No. 3, Sequence I.D. No. 4, or combinations thereof.

6. An isolated DNA sequence, said DNA sequence consisting of the nucleic acid sequence of Sequence I.D. No. 1.

7. An isolated DNA sequence, said DNA sequence consisting of the nucleic acid sequence of Sequence I.D. No. 4.

8. An isolated DNA sequence, said DNA sequence being the intergenic region between the hlyA gene and the hlyB gene and consisting of the nucleic acid sequence of Sequence I.D. No. 3.

* * * * *